(12) United States Patent
Pollack et al.

(10) Patent No.: US 8,685,754 B2
(45) Date of Patent: *Apr. 1, 2014

(54) DROPLET ACTUATOR DEVICES AND METHODS FOR IMMUNOASSAYS AND WASHING

(75) Inventors: Michael G. Pollack, Durham, NC (US); Vamsee K. Pamula, Durham, NC (US); Vijay Srinivasan, Durham, NC (US); Richard B. Fair, Durham, NC (US)

(73) Assignees: Advanced Liquid Logic, Inc., Morrisville, NC (US); Duke University, Durham, NC (US)

( * ) Notice: Subject to any disclaimer, the term of this patent is extended or adjusted under 35 U.S.C. 154(b) by 398 days.

This patent is subject to a terminal disclaimer.

(21) Appl. No.: 12/393,534

(22) Filed: Feb. 26, 2009

(65) Prior Publication Data
US 2009/0263834 A1    Oct. 22, 2009

Related U.S. Application Data

(63) Continuation-in-part of application No. 11/639,531, filed on Dec. 15, 2006, now Pat. No. 8,613,889.

(60) Provisional application No. 61/031,973, filed on Feb. 27, 2008, provisional application No. 60/745,058, filed on Apr. 18, 2006, provisional application No. 60/745,039, filed on Apr. 18, 2006, provisional application No. 60/745,043, filed on Apr. 18, 2006, provisional application No. 60/745,059, filed on Apr. 18, 2006, provisional application No. 60/745,914, filed on Apr. 28, 2006, provisional application No. 60/745,950, filed on Apr. 28, 2006, provisional application No. 60/746,797, filed on May 9, 2006, provisional application No. 60/746,801, filed on May 9, 2006, provisional application No. 60/806,412, filed on Jun. 30, 2006, provisional application No. 60/807,104, filed on Jul. 12, 2006.

(51) Int. Cl.
*G01N 33/553*    (2006.01)

(52) U.S. Cl.
USPC ........... 436/526; 436/518; 436/524; 436/525; 436/164; 435/283.1; 435/287.2; 435/4; 435/7.1

(58) Field of Classification Search
USPC ...................... 436/518, 524, 525, 526, 4, 7.1; 435/283.1, 287.2
See application file for complete search history.

(56) References Cited

U.S. PATENT DOCUMENTS

| | | |
|---|---|---|
| 6,294,063 B1 | 9/2001 | Becker et al. |
| 2005/0106742 A1 | 5/2005 | Wahl |

(Continued)

OTHER PUBLICATIONS

Wang et al., Efficient in-droplet separation of magnetic particles for digital microfluidics, 2007, J. Micromech. MIcroeng., vol. 17, pp. 2148-2156.*

(Continued)

*Primary Examiner* — Melanie Y Brown
(74) *Attorney, Agent, or Firm* — William A. Barrett; Ward & Smith, P.A.

(57) ABSTRACT

Droplet actuator devices and methods for immunoassays and washing are provided. According to one embodiment, a method of providing a droplet in contact with a surface of a super paramagnetic bead with a reduced concentration of a substance is provided and includes: (a) providing a super paramagnetic bead in contact with a droplet comprising a starting concentration and starting quantity of the substance and having a starting volume; (b) conducting one or more droplet operations to merge a wash droplet with the droplet provided in step (a) to yield a combined droplet; and (c) conducting one or more droplet operations to divide the combined droplet to yield a set of droplets. The set of droplets includes: (i) a droplet in contact with the super paramagnetic bead having a decreased concentration of the substance relative to the starting concentration; and (ii) a droplet which is separated from the super paramagnetic bead.

5 Claims, 40 Drawing Sheets

(56) References Cited

U.S. PATENT DOCUMENTS

2006/0254933 A1    11/2006    Adachi et al.
2009/0289213 A1*   11/2009    Pipper et al. ............ 252/62.51 R

OTHER PUBLICATIONS

Weaver, Application of Magnetic Microspheres for Pyrosequencing on a Digital Microfluidic Platform, Aug. 2005, pp. 1-11.*
Jie Ding, "System level architectural optimization of semi-reconfigurable microfluidic system," M.S. Thesis, Duke University Dept of Electrical Engineering, 2000.
Fair, et al., "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.
Moon, Hyejin, Ph.D., "Electrowetting-on-dielectric microfluidics: Modeling, physics, and MALDI application," Ph.D. Dissertation, University of California, Dept. of Mechanical Engineering, Los Angeles, 2006.
Vijay Srinivasan, Vamsee K. Pamula, Richard B. Fair, "An integrated digital microfluidic lab-on-a-chip for clinical diagnostics on human physiological fluids," Lab on a Chip (LOC), vol. 4, pp. 310-315, 2004.
S.C. Terry, J.H. Jerman, and J.B. Angell, " A Gas Chromatographic Air Analyzer Fabricated on a Silicon Wafer," IEEE Transactions on Electron Devices, vol. ED-26, 1979, pp. 1880-1886.
D.B. Tuckerman and R.F.W. Pease, "High-Performance Heat Sinking for VLSI, "IEEE Electron Device Letters, 1981, pp. 126-129.
J.S. Batchelder, " Dielectrophoretic manipulator," Review of Scientific Instruments, vol. 54, 1983, pp. 300-302.
A. Manz, N. Graber, and H.M. Widmer, "Miniaturized Total Chemical Analysis Systems: a Novel Concept for Chemical Sensing," Sensors and Actuators B: Chemical, 1990, pp. 244-248.
W.J.J. Welters and L.G.J. Fokkink, "Fast Electrically Switchable Capillary Effects," Langmuir, vol. 14, Mar. 1998, pp. 1535-1538.
J.C. McDonald, D.C. Duffy, J.R. Anderson, D.T. Chiu, H. Wu, O.J.A. Schuueller, and G.M. Whitesides, "Fabrication of Microfluidic systems in poly (dimethylsiloxane)," Electrophoresis, vol. 21, 2000, pp. 27-40.
A. Wego, S. Richter, L. Pagel, "Fluidic microsystems based on printed circuit board technology," J. Micromech. Microeng., vol. 11, 2001, pp. 528-531.
H. Becker and L.E. Locascio, "Polymer microfluidic devices.," Talanta, vol. 56, Feb. 2002, pp. 267-287.
J.-Y. Yoon and R.L. Garrell, "Preventing Biomolecular Adsorption in Electrowetting-Based Biofluidic Chips," Analytical Chemistry, vol. 75, Oct. 2003, pp. 5097-5102.
P.Y. Chiou, H. Moon, H. Toshiyoshi, C.-J. Kim, and M.G. Wu, "Light actuation of liquid by optoelectrowetting," Sensors and Actuators A: Physical, vol. 104, May. 2003, pp. 222-228.
T.M. Squires and S.R. Quake, "Microfluidics: Fluid physics at the nanoliter scale," Reviews of Modern Physics, vol. 77, Oct. 2005, pp. 977-1026.
Y. Fouillet, D. Jary, A.G. Brachet, C. Chabrol, J. Boutet, P. Clementz, R. Charles, and C. Peponnet, "Design and Validation of a Complex Generic Fluidic Microprocessor Based on EWOD Droplet for Biological Applications," 9th International Conference on Miniaturized Systems for Chemistry and Life Sciences (MicroTAS), Boston, MA: 2005, pp. 58-60.
Z. Guttenberg, H. Muller, H. Habermuller, A. Geisbauer, J. Pipper, J. Felbel, M. Kielpinski, J. Scriba, and A. Wixforth, "Planar chip devices for PCR and hybridization with surface acoustic wave pump.," Lab on a chip, vol. 5, Mar. 2005, pp. 12617-12622.
G.M. Whitesides, "The origins and the future of microfluidics," Nature, vol. 442, 2006, pp. 368-373.
S.M. Langelier, D.S. Chang, R.I. Zeitoun, and M. a Burns, "Acoustically driven programmable liquid motion using resonance cavities.," Proceedings of the National Academy of Sciences of the United States of America, vol. 106, Aug. 2009, pp. 12617-12622.

C.G. Cooney, C-Y. Chen, M.R. Emerling, A Nadim, and J.D. Sterling, Microfluidics and Nanofluidics, vol. 2 Mar. 2006, pp. 435-446.
U.-C. Yi and C.-J. Kim, "Characterization of electrowetting actuation on addressable single-side coplanar electrodes," Journal of Micromechanics and Microengineering, vol. 16, Oct. 2006, pp. 2053-2059.
D. Chatterjee, B. Hetayothin, A.R. Wheeler, D.J. King, and R.L. Garrell, "Droplet-based microfluidics with nonaqueous solvents and solutions.," Lab on a Chip, vol. 6, Feb. 2006, pp. 199-206.
P. Dubois, G. Marchand, Y. Fouillet, J. Berthier, T. Douki, F. Hassine, S. Gmouh, and M. Vaultier, "Ionic Liquid Droplet as e-Microreactor," Analytical Chemistry, vol. 78, 2006, pp. 4909-4917.
M.Madou, J. Zoval, G. Jia, H. Kido, J. Kim, "Lab on a CD," Annual Review of Biomedical Engineering, vol. 8, pp. 601-628.
C.D. Chin, V. Linder, and S.K. Sia, "Lab-on-a-chip devices for global health: past studies and future opportunities.," Lab on a Chip, vol. 7, Jan. 2007, pp. 41-57.
R.Baviere, J. Boutet, and Y. Fouillet, " Dynamics of droplet transport induced by electrowetting actuation," Microfluidics and Nanofluidics, vol. 4, May 2007, pp. 287-294.
S.-Y. Teh, R. Lin, L.-H. Hung, and A.P. Lee, " Droplet microfluidics.," Lab on a chip, vol. 8 Feb. 2008, pp. 198-220.
A. Huebner, S. Sharma, M. Srisa-Art, F. Hollfelder, J.B. Edel, and A.J. DeMello, "Microdroplets: a sea of applications?," Lab on a Chip, vol. 8, Aug. 2008, pp. 1244-1254.
P. Yager, T. Edwards, E. Fu, K. Helton, K. Nelson, M.R. Tam, and B.H. Weigl, "Microfluidic diagnostic technologies for global public health," Nature, vol. 442, 2006, pp. 412-418.
J. Gong and C.-J.C. Kim, "Direct-referencing two-dimensional-array digital microfluidics using multi-layer printed circuit board," Journal of Microelectromechanical Systems, vol. 17, Jan. 2008, pp. 257-264.
P.Y. Paik, V.K. Pamula, and K. Chakrabarty, "A Digital-Microfluidic Approach to Chip Cooling," IEEE Design & Test of Computers, vol. 25, Jul. 2008, pp. 372-381.
E.M. Miller and A.R. Wheeler, "A Digital Microfluidic Approach to Homogeneous Enzyme Assays," Analytical Chemistry, vol. 80, 2008, pp. 1614-1619.
R.S. Sista, A.E. Eckhardt, V. Srinivasan, M.G. Pollack, S. Palanki, and V.K. Pamula, "Heterogeneous immunoassays using magnetic beads on a digital microfluidic platform," Lab on a Chip, vol. 8, Dec. 2008, pp. 2188-2196.
L. Luan, R.D. Evans, N.M. Jokerst, and R.B. Fair, "Integrated Optical Sensor in a Digital Microfluidic Platform," IEEE Sensors Journal, vol. 8, May. 2008, pp. 628-635.
R. Sista, Z. Hua, P. Thwar, A Sudarsan, V. Srinivasan, A Eckhardt, M. Pollack, and V. Pamula, "Development of a digital microfluidic platform for point of care testing.," Lab on a chip, vol. 8, Dec. 2008, pp. 2091-2104.
I. Barbulovic-Nad, H. Yang, P.S. Park, and A.R. Wheeler, "Digital microfluidics for cell-based assays.," Lab on a chip, vol. 8, Apr. 2008, pp. 519-526.
R. Mariella, "Sample preparation: the weak link in microfluidics-based biodetection.," Biomedical Microdevices, vol. 10, Dec. 2008, pp. 777-784.
Luk, V.N., Pluronic additives: a solution to sticky problems in digital microfluidics.,: Langmuir: the ACS journal of surfaces ans colloids, vol. 24, Jun. 2008, pp. 6382-6389.
D. Brassard': L. Malic, F. Normandin, M. Tabrizian, and T. Veres, "Water-oil core-shell droplets for electrowetting-based digital microfluidic devices.," Lab on a chip, vol. 8, Aug. 2008, pp. 1342-1349.
R. Mukhopadhyay, "Microfluidics: on the slope of enlightenment.," Analytical chemsitry vol. 81, Jun. 2009, pp. 4169-4173.
J.L. Poulos, W.C. Nelson, T.-J. Jeon, C.-J. "CJ" Kim, and J.J. Schmidt, "Electrowetting on dielectric-based microfluidics for integrated lipid bilayer formation and measurement," Applied Physics Letters, vol. 95, 2009, p. 013706.
Pollack et al., "Electrowetting-Based Actuation of Droplets for Integrated Microfluidics," Lab on a Chip (LOC), vol. 2, pp. 96-101, 2002.
M.J. Jebrail and A.R. Wheeler, "Lets get digital: digitizing chemical biology with microfluidics.," Current Opinion in Chemical Biology, vol. 14, Oct. 2010, pp. 574-581.

* cited by examiner

DROPLET ACTUATOR DEVICES AND METHODS FOR IMMUNOASSAYS AND WASHING

1 RELATED APPLICATION

This application claims benefit of U.S. Provisional Application 61/031,973, filed Feb. 27, 2008; and is a continuation-in-part of U.S. application Ser. No. 11/639,531, filed Dec. 15, 2006 now U.S. Pat. No. 8,613,889, which claims benefit of U.S. Provisional Application 60/745,058, filed Apr. 18, 2006, and claims benefit of U.S. Provisional Application 60/745,039, filed Apr. 18, 2006, and claims benefit of U.S. Provisional Application 60/745,043, filed Apr. 18, 2006, and claims benefit of U.S. Provisional Application 60/745,059, filed Apr. 18, 2006, and claims benefit of U.S. Provisional Application 60/745,914, filed Apr. 28, 2006, and claims benefit of U.S. Provisional Application 60/745,950, filed Apr. 28, 2006, and claims benefit of U.S. Provisional Application 60/746,797, filed May 9, 2006, and claims benefit of U.S. Provisional Application 60/746,801, filed May 9, 2006, and claims benefit to U.S. Provisional Application 60/806,412, filed Jun. 30, 2006, and claims benefit of U.S. Provisional Application 60/807,104, filed Jul. 12, 2006, the disclosures of which are incorporated by reference in their entirety.

2 GRANT INFORMATION

This invention was made with government support DK066956-02 and GM072155-02 awarded by the National Institutes of Health of the United States. The government has certain rights in the invention.

3 FIELD OF THE INVENTION

The present invention broadly relates to performing an immunoassay on a lab-on-a-chip using a droplet-based approach, particularly involving magnetically responsive beads using droplet-based transport. Embodiments of the present invention relate to droplet actuator devices and methods for immunoassays and washing.

4 BACKGROUND OF THE INVENTION

Droplet actuators are used to conduct a wide variety of droplet operations. A droplet actuator typically includes two plates separated by a space. The plates include electrodes for conducting droplet operations. The space is typically filled with a filler fluid that is immiscible with the fluid that is to be manipulated on the droplet microactuator. Surfaces exposed to the space are typically hydrophobic. There is a need in the art for immunoassays to be performed in a droplet actuator. The immunoassays may include magnetic beads. Further, there is a need for improved methods of effectively washing magnetic beads for use in magnetic immunoassays.

5 BRIEF DESCRIPTION OF THE INVENTION

Embodiments of the present invention relate to droplet actuator devices and methods for immunoassays and washing.

According to one embodiment, a method of providing a droplet in contact with a surface of a super paramagnetic bead with a reduced concentration of a substance is provided and comprises: (a) providing a super paramagnetic bead in contact with a droplet comprising a starting concentration and starting quantity of the substance and having a starting volume; (b) conducting one or more droplet operations to merge a wash droplet with the droplet provided in step (a) to yield a combined droplet; and (c) conducting one or more droplet operations to divide the combined droplet to yield a set of droplets. The set of droplets comprises: (i) a droplet in contact with the super paramagnetic bead having a decreased concentration of the substance relative to the starting concentration; and (ii) a droplet which is separated from the super paramagnetic bead.

According to another embodiment, a method of detecting insulin in a sample is provided and comprises: (a) executing droplet operations to combine affinity-based assay reagents on a droplet microactuator with a sample potentially comprising the insulin to generate a signal indicative of the presence, absence and/or quantity of insulin; and (b) detecting the signal, wherein the signal corresponds to the presence, absence and/or quantity of the insulin in the sample.

According to yet another embodiment, a method of detecting IL-6 in a sample is provided and comprises: (a) executing droplet operations to combine affinity-based assay reagents on a droplet microactuator with a sample potentially comprising the IL-6 to generate a signal indicative of the presence, absence and/or quantity of IL-6; and (b) detecting the signal, wherein the signal corresponds to the presence, absence and/or quantity of the IL-6 in the sample.

6 DEFINITIONS

As used herein, the following terms have the meanings indicated.

"Activate" with reference to one or more electrodes means effecting a change in the electrical state of the one or more electrodes which results in a droplet operation.

"Analyte," means a target substance for detection which may be present in a sample. Illustrative examples include antigenic substances, haptens, antibodies, proteins, peptides, amino acids, nucleotides, nucleic acids, drugs, ions, salts, small molecules, and cells.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. The beads may include one or more populations of biological cells adhered thereto. In some cases, the biological cells are a substantially pure population.

In other cases, the biological cells include different cell populations, e.g., cell populations which interact with one another.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading.

"Surface" with reference to immobilization of a molecule, such as an antibody or in analyte, on the surface, means any surface on which the molecule can be immobilized while retaining the capability to interact with droplets on a droplet actuator. For example, the surface may be a surface on the droplet actuator, such as a surface on the top plate or bottom plate of the droplet actuator; a surface extending from the top plate or bottom plate of the droplet actuator; a surface on a physical object positioned on the droplet actuator in a manner which permits it to interact with droplets on the droplet actuator; and/or a bead positioned on the droplet actuator, e.g., in a droplet and/or in a droplet actuator but exterior to the droplet.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Washing" with respect to washing a magnetically responsive bead means reducing the amount and/or concentration of one or more substances in contact with the magnetically responsive bead or exposed to the magnetically responsive bead from a droplet in contact with the magnetically responsive bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Other embodiments are described elsewhere herein, and still others will be immediately apparent in view of the present disclosure.

The terms "top" and "bottom" are used throughout the description with reference to the top and bottom substrates of the droplet actuator for convenience only, since the droplet actuator is functional regardless of its position in space.

When a given component, such as a layer, region or substrate, is referred to herein as being disposed or formed "on" another component, that given component can be directly on the other component or, alternatively, intervening components (for example, one or more coatings, layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitations relating to particular methods of material transport, deposition, or fabrication.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

7 BRIEF DESCRIPTION OF THE DRAWINGS

8 DETAILED DESCRIPTION OF THE INVENTION

A generic architecture is developed to perform an immunoassay on a lab-on-a-chip using a droplet-based approach. The lab-on-a chip designed is used to establish the proof of concept of performing an immunoassay involving magnetically responsive beads using droplet based transport. Fabrication of the designed lab-on-a-chip is discussed and the testing of the fabricated chip with the magnetic beads and the reagents used in the immunoassay. Furthermore, the detection instrumentation used for measurement of chemiluminescence is also described.

As discussed herein, International Patent Application No. PCT/US 06/47486 to Pollack et al., filed on Dec. 11, 2006, entitled "Droplet-Based Biochemistry," and International Patent Application No. PCT/US 08/53545 to Sista et al., filed on Feb. 11, 2008, entitled "Droplet Actuator Devices and Methods Employing Magnetic Beads" include disclosures relating to bead handling and washing and are each incorporated herein by reference.

8.1 Lab-on-a-Chip Specifications

The basic requirements to perform an immunoassay on a droplet based system are described in this section. The functional components of the lab-on-a-chip are the droplet generation units and droplet pathways for transport, mixing, incubation and washing of the magnetic beads which is the most important step to perform a magnetic immunoassay.

8.1.1 Design of the Reservoir and the Droplet Pathways

Figure 1:
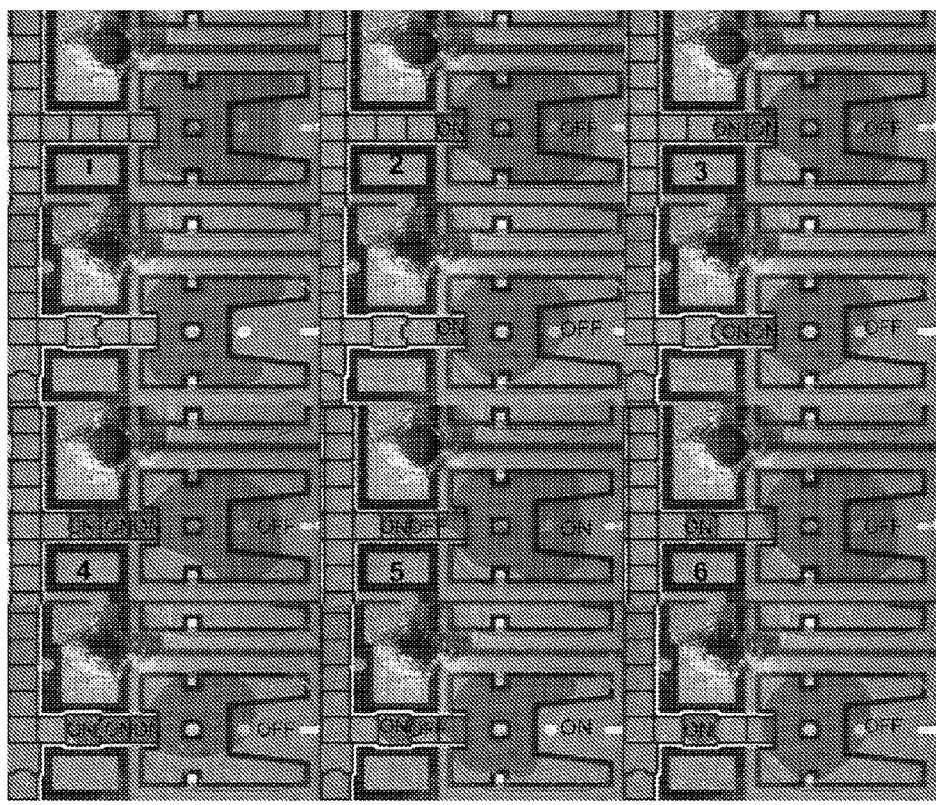
FIG. 1 is an illustration depicting the various stages in dispensing of a droplet from a reservoir.

Design of a lab-on-a-chip used to perform a glucose assay was already described by Srinivasan et al. [2005] wherein the design of the electrode for the reservoir has been described. FIG. 1 depicts the various stages in dispensing of a droplet from the reservoir. Dispensing occurs in the following three steps [Ren, 2003].

1. A liquid column is extruded from the reservoir by activating a series of electrodes adjacent to it as shown in FIG. 1.
2. Once the column overlaps the electrode where the droplet is to be formed, all the remaining electrodes are deactivated to form a neck in the column.
3. The electrode in the reservoir is then activated to pull back the liquid causing the neck to break completely and form a droplet almost equal to the size of the electrode.

The reservoir electrode in this design has a tapering-pull back electrode (wider at the dispensing end) to ensure that the liquid always stayed at the dispensing end of the reservoir. The various parameters that would affect the reproducibility and reliability of the dispensing process are the reservoir shape and size, shape and size of the pull back electrode, size of the unit electrode which would decide the size of the unit droplet and the spacer thickness which would decide the volume of each droplet. The choice and effect of each of these parameters is discussed in the below [Ren, 2004].

1. Electrode size—The electrode size is chosen to be 1250 µm because of the sensitivity required in immunoassays. However the electrode pitch can be reduced once the proof of concept of an immunoassay on lab-on-a-chip has been established. The electrode size may be altered as well.
2. Spacer thickness—Previous results [Ren, 2003; Cho, 2003] indicate that the droplet dispensing for a water-silicone oil system requires a droplet aspect ratio (diameter: height) greater than or equal to 5. However to transport droplets containing magnetic beads and to immobilize magnetic beads within a droplet the gap height may be >250 µm for efficient attraction of the beads. Hence a gap height of 300 µm is chosen. For this electrode pitch and gap height the volume of each unit droplet would be approximately 500 nL. This would also provide enough sensitivity for very low concentration of analytes. The height, volume, and pitch may be altered.

Figure 2:
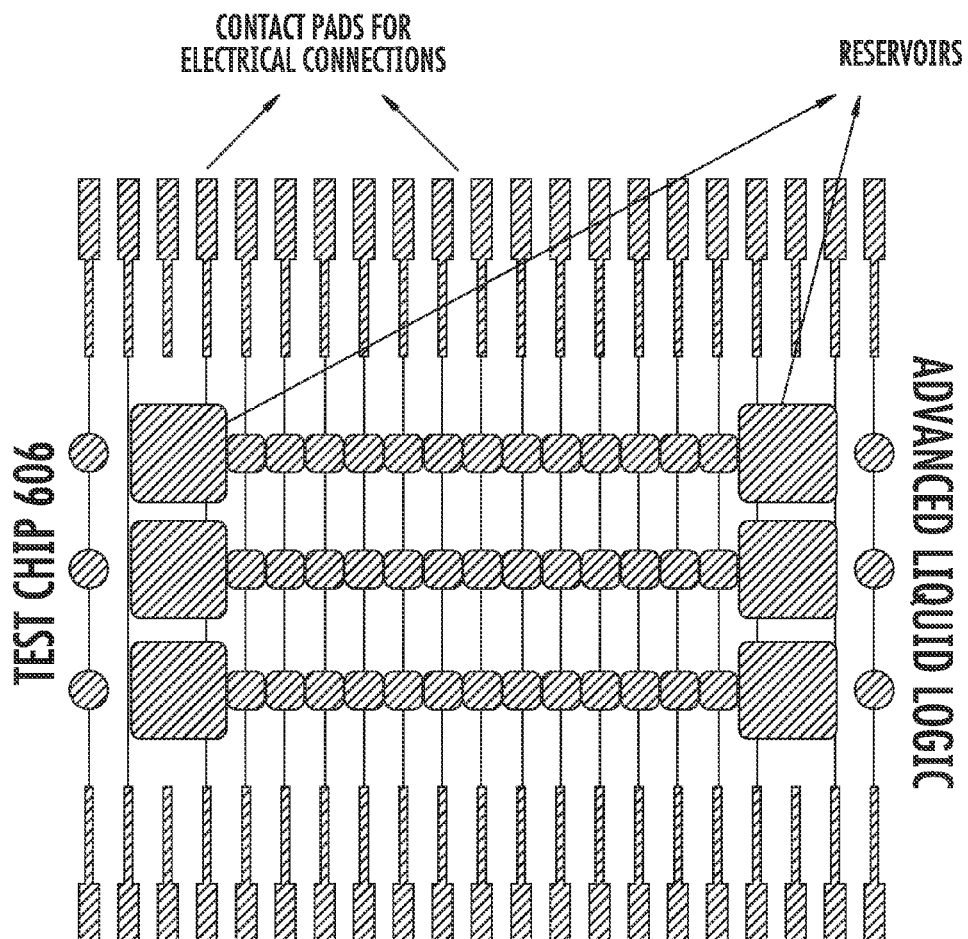
FIG. 2 is an illustration of a basic design of a droplet-based chip for performing washing protocols and magnetic immunoassays.

Apart from the above design parameters discussed above, other parameters which may affect dispensing and transport of the liquid include voltage applied and the volume of the liquid pipetted onto the lab-on-a-chip. Furthermore the number of electrodes in a single array is another important parameter to perform a magnetic immunoassay on chip. The minimum number of electrodes required for efficient washing of the magnetic beads which involves asymmetric splitting of long slugs of supernatant is 10 in a single array. FIG. 2 shows a basic design of a droplet based electrowetting chip to perform a magnetic immunoassay. FIG. 2 shows the complete chip design used to develop the washing protocols and to perform the magnetic immunoassay.

8.2 Fabrication of Lab-on-a-Chip and System Assembly
8.2.1 Chip Fabrication

The electrowetting chips were fabricated using a commercially available photomask manufacturing process. Electrode patterns were photolithographically imaged and etched on a chrome-coated photomask blank. The base material was 0.060" thick soda lime glass and the thickness of the chrome layer was 840 A. Photosciences Inc., Torrance, Calif. was used as the vendor to fabricate the chips.

Parylene C was used as the dielectric on all the chips. The Parylene C coating process is a conformal vapor deposition process which produces a high-quality pinhole free dielectric layer. The Parylene C was coated at the SMIF Facility at Duke University, Durham, N.C. or Paratronix Inc, MA.

Teflon AF was used as the hydrophobic coating on all the chips. Teflon AF is a amorphous fluoropolymer which is soluble in perfluorinated solvents making it suitable for application as thin films by either dip coating or spin coating. A 200 nm-1000 nm thick Teflon AF layer was typically used as the hydrophobic coating on the electrowetting chips. Indium-tin-oxide (ITO) coated glass plates were used as the cover plates to create the droplet sandwich. The ITO plates were also coated with a thin layer of Teflon AF.

8.2.2 Top Plate Fabrication

An indium-tin oxide or poly-carbonate plastic acted as the ground plane. The indium-tin oxide slides were obtained from Delta technologies. Polycarbonate plastic pieces were coated with ITO by Genvac Aerospace. Holes were drilled in the ITO coated top plate such that they align with the reservoirs of the chip. The top plates were later cleaned by sonicating in Isopropanol and then air dried. The ITO plates were hydrophobized by spin coating or dip coating (<100 nm thick film) with 1% Teflon AF. The glass plates were then baked at 180° C. for 45 minutes to remove the solvent.

8.2.3 System Assembly

The electrowetting chip and the top plate were assembled such that the holes on the top plate were aligned. The chip and the top plate were clamped and held down by microscope clips on the sides of the top plate. A gap height of 300 µm was used which was created by placing a 300 µm shim in between the top plate and the chip. Electrical connections to the contacts were made using a 22-pin SOIC test clip (Pomona electronics). Voltages were applied to the test clip using an electronic controller which was essentially an array of high-voltage switches. The state of the switches (ON or OFF) was controlled by custom written software through the parallel port or USB port of the computer.

8.3 Detection Instrumentation

Detection in electrowetting can be done using optical techniques because of the transparent nature of the materials involved in the chip. Srinivasan et al. [2005] developed an optical absorbance measurement system consisting of an LED and a photodiode which is integrated with the electrowetting device to monitor the color obtained during the glucose assays. However for the immunoassays since the concentrations to be detected are very low and such low levels of color cannot be detected. Although measurement of fluorescence is a good method of detection, setting up of such a detection technique integrated to the electrowetting device is difficult. The other detection technique that is most commonly used for measuring the concentrations of analytes in immunoassays is chemiluminescence. Chemiluminescence is the emission of light without emission of heat as a result of a chemical reaction.

Figure 3:
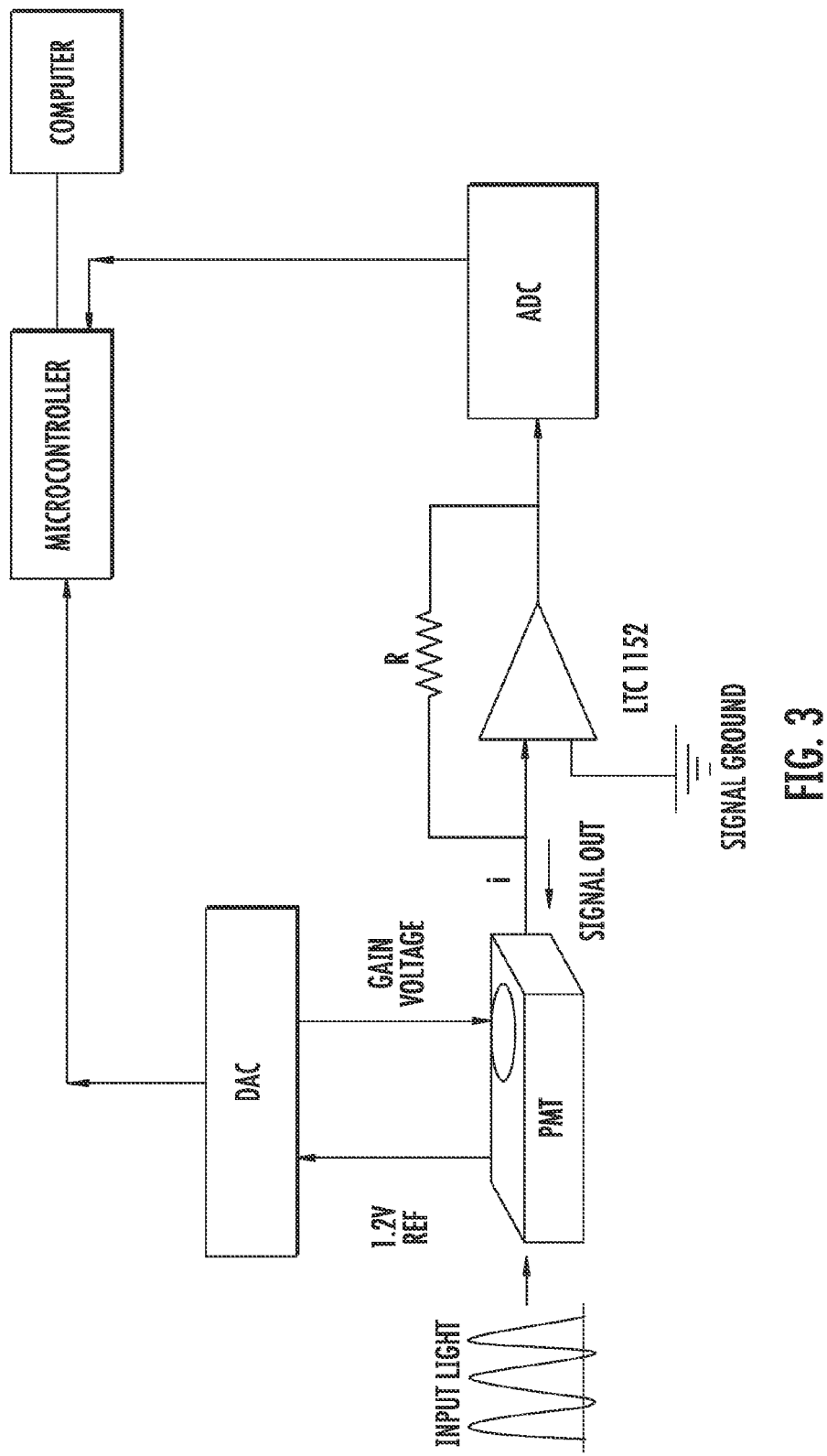
FIG. 3 is an illustration scheme for a droplet actuator system.

The decay of the excited state to a lower energy level is responsible for the emission of light. Light detection technology is a powerful tool that provides deeper understanding of more sophisticated phenomena. Measurement of light offers unique advantages: for example non destructive analysis of a substance, high speed performance and extremely high detectability. Recently in particular, such advanced fields as scientific measurement, medical diagnosis and treatment, high energy physics, spectroscopy and biotechnology require development of photodetectors that exhibit the ultimate in various performance parameters. Photodetectors or light sensors can be broadly classified into three major categories based on their operating principle: external photoelectric effect, internal photoelectric effect and thermal types. The external photoelectric effect is a phenomena in which when light strikes a metal or semiconductor placed in a vacuum, electrons are emitted from its surface into the vacuum. Photomultiplier tubes (often abbreviated as PMT) make use of this external photoelectric effect (shown in FIGS. 3, 4, and 5) and are superior in response and sensitivity (low-light level detection). Hamamatsu's PMT (cat #9858) is used for this research to detect the chemiluminescence released during the immunoassays. In the DC mode of operating the PMT, the DC components from the PMT are detected by means of an amplifier and a low pass filter. The connection circuit used to detect the chemiluminescence is shown in FIG. 5.

8.4 Testing of Fabricated Lab-on-a-Chips 8.4.1 Biocompatibility of the Lab-on-a-Chips The fabricated lab-on-a-chips were tested with a wide range of reagents that will be used to perform the magnetic immunoassay. An extensive list of the reagents tested on the lab-on-a-chip is presented.

1. Antibodies for Insulin and Interleukin-6 (IL-6)
2. Different concentrations of Insulin and IL-6
3. Magnetically responsive beads
4. Different concentrations of Tween® 20
5. Different concentrations of Triton X 15
6. Different concentrations of Bovine serum albumin (BSA)
7. Serum
8. Different concentrations of Horse radish peroxidase (HRP) enzyme
9. Different concentrations of Alkaline phosphatase (ALP) enzyme
10. Lumigen APS-5 (chemiluminescent substrate for ALP enzyme)
11. Lumigen Ultra PS-Atto (Chemiluminescent substrate for HRP enzyme)

Experimental protocol for testing—1 µL of the reagent is pipetted manually on to one of the electrodes on the lab-on-a-chip and is sandwiched using an ITO top plate for grounding. The gap height used was 300 µm which was filled with 1.5 cSt Silicone oil. The droplet was transported across 5 electrodes to and fro at different frequencies and different voltages until the droplet stops to transport completely.

Figure 6:
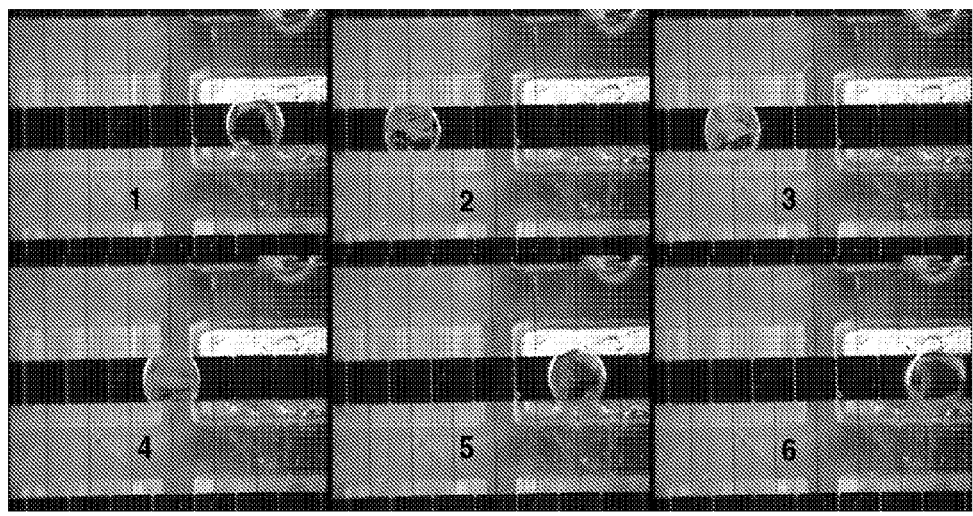
FIG. 6 is an illustration depicting transport of a unit droplet containing magnetically responsive beads.

Observations—The reagents mentioned above are proteins and surfactants and have a lower surface tension when compared to water. Hence they have the tendency to adsorb to the surface of the chip and render the chip to be permanently hydrophilic. It was observed that different voltages were required for different solutions based on the surface tension. Furthermore, solutions transported well at higher frequencies. This is because, the higher the residence time of a droplet on an electrode, the higher is the adsorption of the proteins onto the surface. However the oil film and the interfacial tension of the droplet-oil interface is yet to be characterized extensively for different reagents. The maximum concentration of BSA, HRP that were transportable was 10 mg/mL and 5 mg/mL respectively. The magnetically responsive beads transported really well on the droplet based lab-on-a-chip. FIG. 6 shows the transport of the magnetically responsive beads being transported across five electrodes with a magnet underneath the electrodes to attract the magnets. In stage 1 (FIG. 6), the beads were aggregated because of the effect of the magnetic field, however they were completely resuspended after a complete cycle of transport over five electrodes (stage 4 in FIG. 6).

The maximum concentration of Tween® 20 in Phosphate buffered saline (PBS) that was transportable without major difficulty was 0.005%. However, the magnetically responsive beads required 0.01% of Tween® 20 in the supernatant for efficient resuspension in the droplet. Hence 0.1% Triton X 15 was added to the 1.5 cSt silicone oil and was used as the filler medium. This improved the transportability of all the proteins mentioned above by stabilizing the oil film between the droplet and the surface of the chip. 0.01% Tween® 20 was also transportable with 1.5 cSt silicone oil with 0.1% Triton® 100.

Hence the compatibility of the electrowetting system with biological samples validated by the results and discussion presented above. Pure protein solutions, droplets with surfactants, physiological samples such as serum and plasma were transportable.

8.4.2 Material Defects

Figure 7:
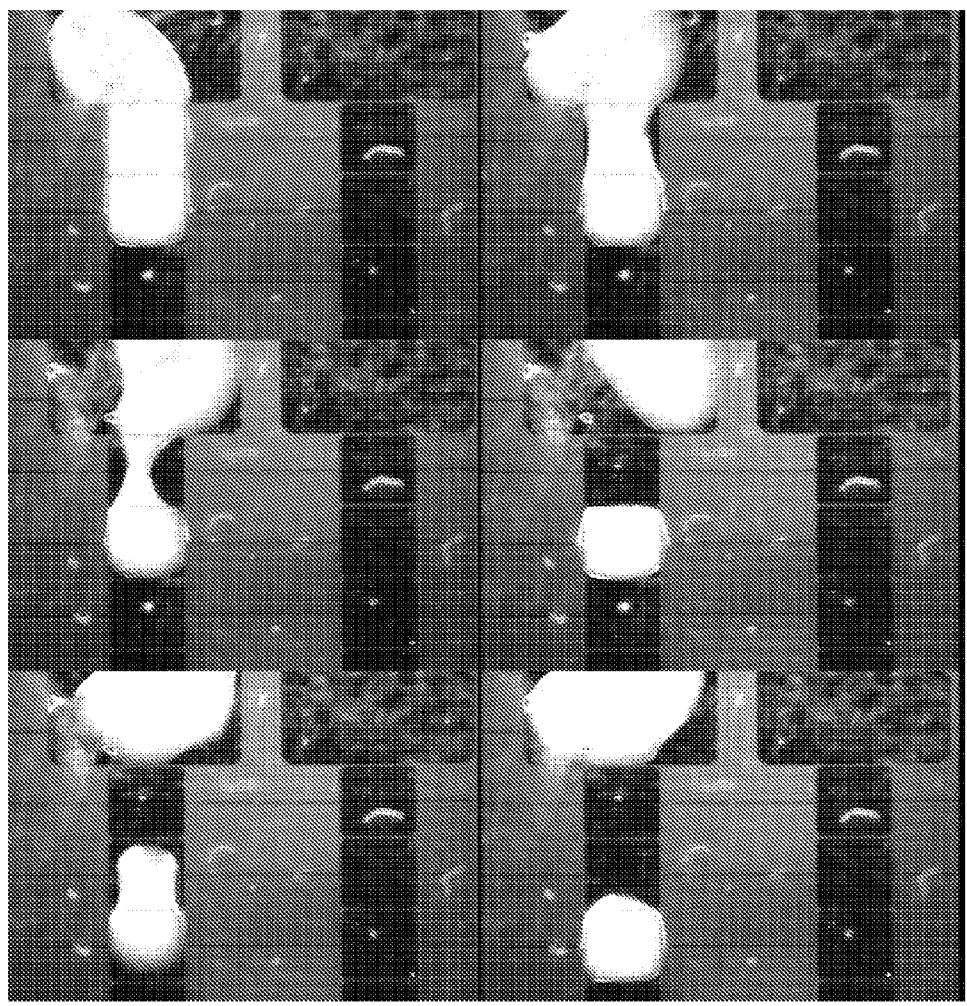
FIG. 7 is an illustration depicting dispensing and transport of serum on a test chip.
Figure 8A:
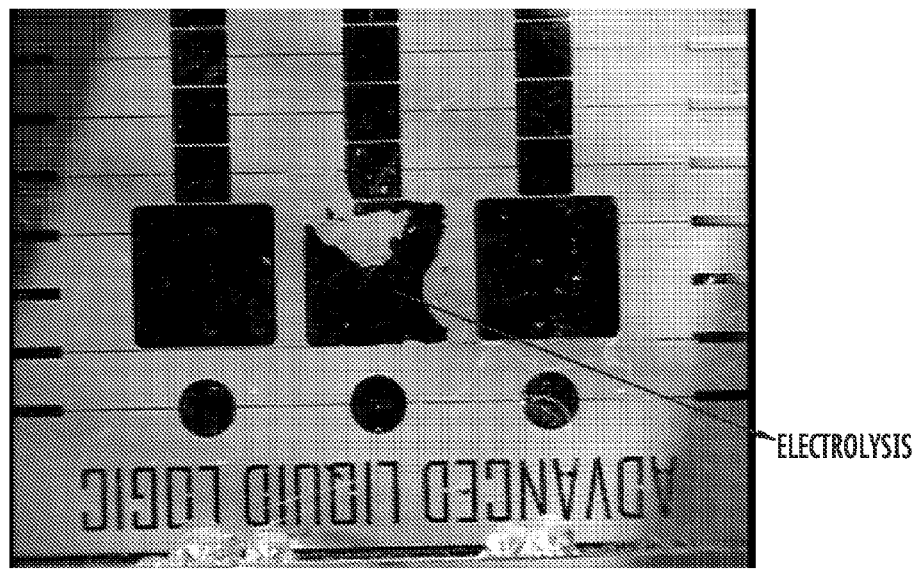
FIGS. 8A and 8B are illustrations depicting electrolysis in a reservoir and electrolysis at the point of splitting, respectively.
Figure 8B:
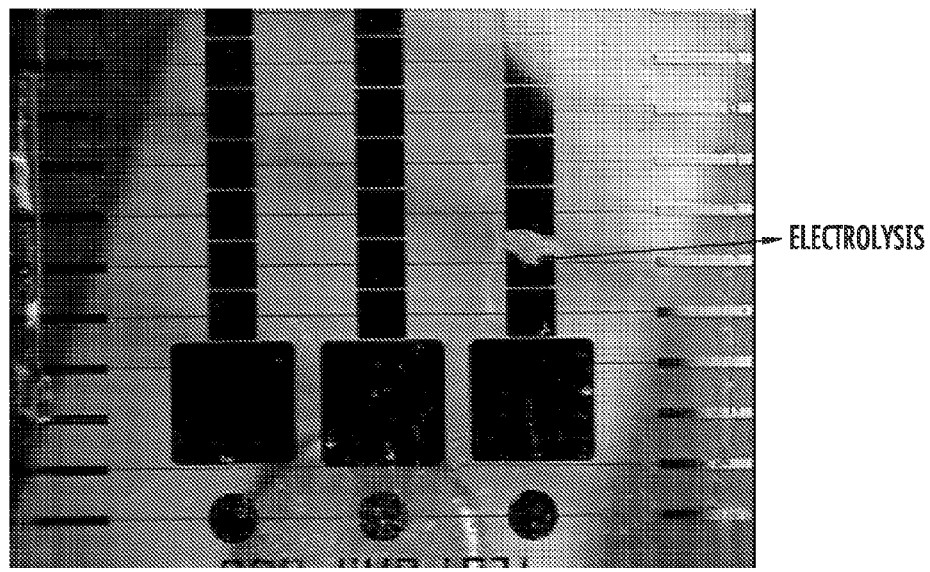
Figure 9:
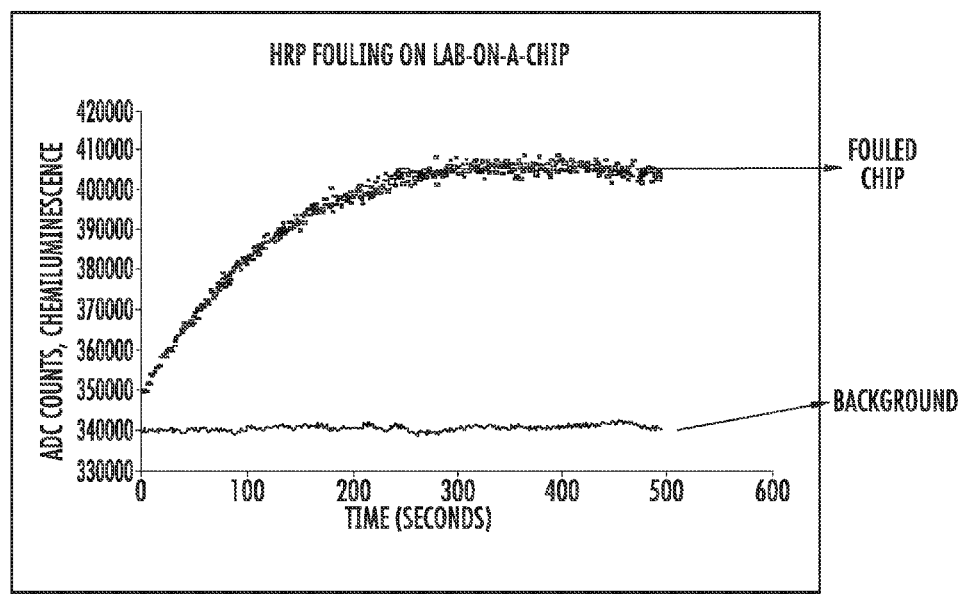
FIG. 9 is a graphical representation of HRP fouling on lab-on-a-chip.

The thickness of the parylene coating and the concentration of Teflon AF used in the fabrication of the droplet based lab-on-a-chip were 5 µm and 1% respectively. The main reliability concern in the chips was the parylene insulator. Electrolysis in the chips due to insulator was eventually seen in all the chips exclusively in the reservoir and at the point of splitting (FIG. 7). Though the exact reason for the breakdown is unknown at this time it is hypothesized that this is due to the mechanical cracking or failure of the parylene film at the gasket-electrode junction in the reservoir which exposes the metal to liquid and causes electrolysis. This eventual breakdown of the insulator limited the time duration of single automated experiments. The experiments lasted only for 10 minutes.

Hence the next batch of chips were coated with 12 µm parylene and dip coated with 6% Teflon AF. This solved the electrolysis problem and the chips lasted for more than one hour without any electrolysis. However the problem of protein fouling still persists. Hence a new chip was used for every different experiment.

8.4.3 Protein Fouling on Chips

It was explained by Srinivasan et al. [2004] that the proteins contaminate the surface of the chip and makes them permanently hydrophilic. Hence the following experiment was performed to quantify the amount of contamination.

Figure 4:
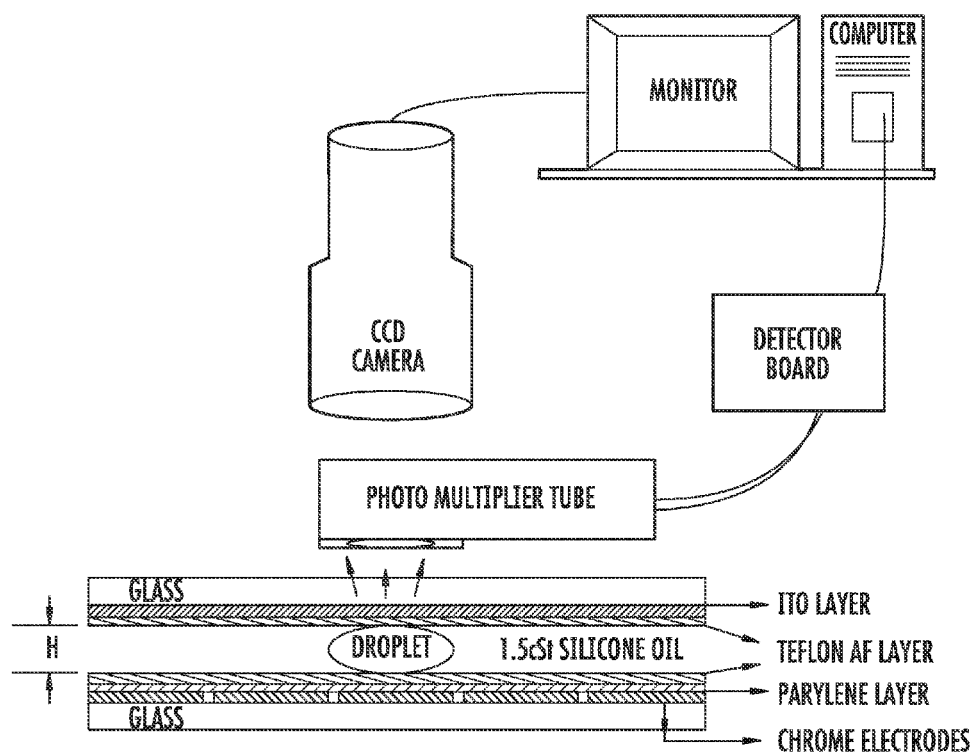
FIG. 4 is an illustration of a chemiluminescent detection setup.
Figure 5:
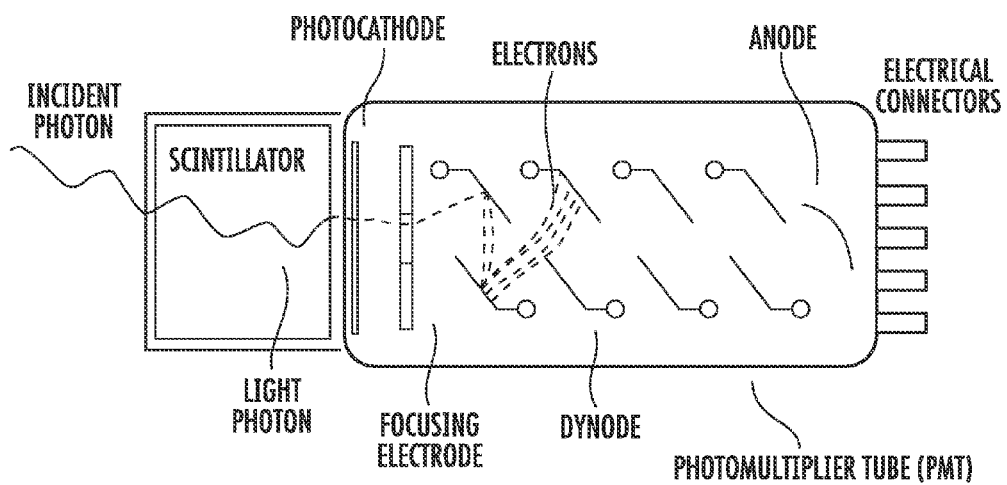
FIG. 5 is an illustration of a connection circuit used to detect chemiluminescence.

Materials—1 mg/mL HRP, Lumigen Ultra PS atto (chemiluminescent substrate for HRP enzyme), 1.5 cSt silicone oil, Test chip 606 coated with 12 µm parylene and dip coated with 6% Teflon AF, ITO top plate dip coated with Teflon AF, chemiluminescent detection setup (FIG. 4).

Methods—1 µL of 1 mg/mL HRP was manually pipetted on an electrode on the fabricated lab-on-a-chip and sandwiched using an ITO coated top plate which acts as the ground plane. The gap height used was 300 µm which was filled with 1.5 cSt silicone oil. The droplet was transported over three electrodes for 30 minutes and is discarded. To quantify the amount of enzyme that was being deposited on the electrodes, 1 µL of Lumigen Ultra PS atto and transported once over the same three electrodes over which the HRP was transported and parked on one of the electrodes. The chemiluminescence was measured for 500 seconds and compared to the background. It was observed that there was significant increase in the chemiluminescent signal which confirms the proposition that proteins adsorb to the hydrophobic surface. Hence new chips and new electrode lines were used for each separate experiment.

8.5 Immunoassay Description

An immunoassay is a biochemical test that measures the concentration of a protein or hormone in a physiological liquid like blood, serum or urine. Immunoassays benefit from the very high selectivity and affinity of antibody/antigen systems, as well as from decades of immunoassay developments in diagnostics. The detection of the concentration of the antibody or the antigen can be achieved by variety of methods. One of the most common is to label the antigen or antibody with an enzyme (Enzyme linked immunoassay), radio isotopes (Radio immunoassay) or fluorescence. Other techniques include agglutination, nephelometry, turbidimetry and western blot. Immunoassays are classified as homogenous and heterogeneous assays. In a homogenous immunoassay also called competitive immunoassay the antigen in the unknown sample competes with the labeled antigen to bind to the antibodies. The amount of labeled antigen to the antibodies is then measured by different detection techniques mentioned above. The response or signal measured is inversely proportional to the concentration of the antigen in the unknown. This is because the greater the response, the less antigen in the unknown was able to "compete" with the labeled antigen for binding with the antibodies.

Figure 10:
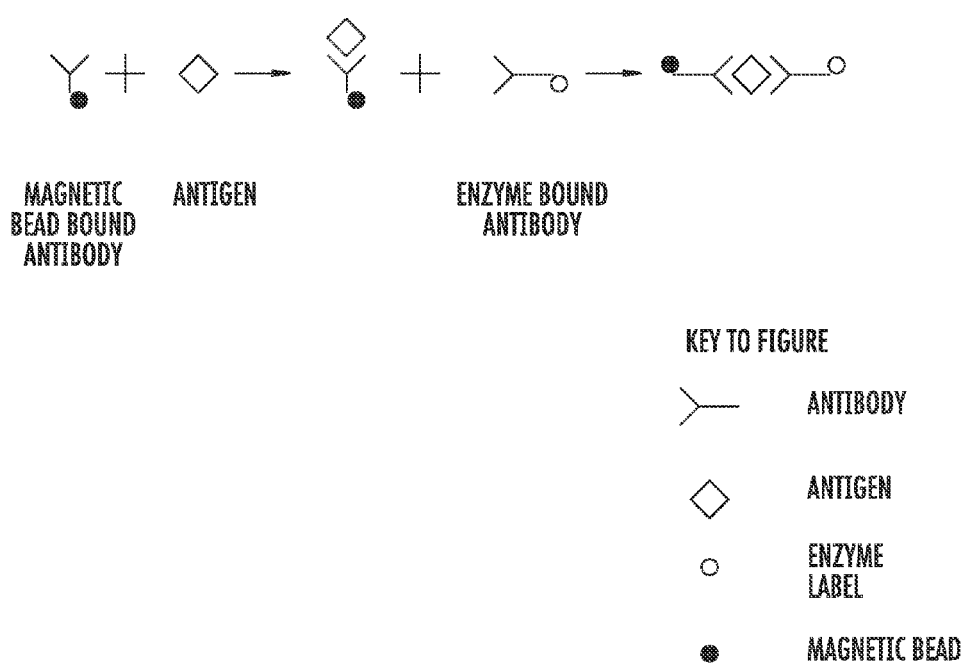
FIG. 10 is a schematic representation of a magnetic immunoassay involving a "sandwich" complex with an antigen coupled between a primary and secondary antibody.

In a heterogeneous immunoassay also referred to as the "sandwich assay" requires the formation of "sandwich" complex with an antigen coupled between a primary and secondary antibody as shown in FIG. 10. The primary antibody is immobilized onto a solid surface which may be typically a plate or the surface of a tube or beads made of various materials which provide a vast surface area. The secondary antibody is labeled with an enzyme which reacts with a substrate or an introduced chemical reagent to give a relative indication of the concentration of the antigen (the extent of the reaction is a relative measure of the concentration of the antigen). The antigen of interest is captured between the two antibodies which can further be separated from the unreacted solution and analyzed. A heterogeneous immunoassay includes an extra step of removing the excess or unbound antibody or antigen from the reaction site, using a solid phase reagent which may be the solid wall of a tube or a plate or beads made of various materials. The immunoassay which utilizes magnetically responsive beads or spheres as the solid phase is termed as "magnetic immunoassay". Performing the above described magnetic immunoassay on chip involves three basic steps: (i) affinity capture, (ii) separation and (iii) detection. Out of the three steps to perform the immunoassay on chip, the separation step which separates the magnetic beads with the antibody-antigen complex from the excess/unreacted reagents is an important and difficult operation to perform on chip. The washing step involves immobilizing the magnetically responsive beads at a single place and removes most of the excess/unreacted supernatant. This process has to be repeated until there is substantially no signal from the supernatant.

The washing step has to be done in such a way as to:

Avoid permanent clumping or aggregation of the magnetic beads;

During a droplet splitting operation, capture and immobilize substantially all of the magnetically responsive beads within a single droplet;

Ensure immobilization and retention of substantially all of the magnetically responsive beads during the washing operation; and Upon completion of washing process, ensure resuspension of all of the magnetic beads within the droplet with no significant clumping or aggregation of the beads.

There are various parameters that control the efficiency of washing the magnetic beads which would further influence the result of the immunoassay. There is a need for improved methods of washing the magnetic beads.

8.6 Super Paramagnetic Beads

Encapsulated super paramagnetic beads have found novel applications in the field of biomedicine, drug delivery, cell separation and molecular biology [Technote #101, 1999; Technote #301, 1999]. These super paramagnetic beads have the unique property of not retaining any magnetism once the magnetic field is removed. This unique feature of these magnetic beads makes it a candidate for use as the solid phase in an immunoassay. The advantages of the magnetic immunoassay are:

Separation is simple and fast;
Separation can be done with the basic lab equipment;
Can be used to determine fairly low antigen concentrations because of high surface area available for binding on the magnetic beads; and
Adaptability to automation.

Super paramagnetic beads used for immunoassay are generally available in different sizes ranging from a about few hundreds of microns to nanometers. They are available labeled with different proteins, enzymes and antibodies useful for different applications in the immunoassay.

8.7 Parameters Involved in Washing of Magnetic Beads

The basic parameters involved in washing the magnetic beads on chip are:

Buffer in which the beads are suspended;
Magnetic field strength applied to immobilize the beads;
Position of the magnet with respect to the droplet; and
Concentration of the magnetic bead suspension.

Each of these parameters was explored to establish a standard washing protocol to ensure very good washing efficiency with minimal bead loss. High wash efficiency implies that there is no or very less excess enzyme left in the supernatant which would produce a secondary signal.

8.7.1 Buffer System

The buffer system in which the magnetically responsive beads are suspended plays a very important factor in the bead mobilization. Different types of buffers with varied concentrations of salt and surfactant were used to suspend the magnetic beads and the attraction and aggregation of beads were studied under magnetic field. The following buffers were used to suspend the magnetic beads:

Phosphate buffered saline (PBS)
Tris buffered saline (TBS)
PBS and TBS with Bovine serum albumin (BSA)
PBS and TBS with 0.005% Tween® 20
PBS and TBS with 0.01% Tween® 20

Materials—BioMAG streptavidin coated magnetic beads (cat #BM 551) obtained from Bang's Laboratories (Diameter—2.8 µm) and Dynal® MyOne™ Streptavidin (Diameter—1.05 µm) (cat #650.01) obtained from Dynal Biotech were used for this study. Tween® 20 was obtained from Pierce. Stock solution of BSA (10 mg/ml) was provided by Glaxo Smithkline (Durham, N.C.) and diluted to 1 mg/ml, 0.1 mg/ml and 0.01 mg/ml in PBS and TBS.

Experimental setup—Aliquots of the stock solution of the BioMAG streptavidin coated magnetic beads were taken and diluted 4 times using the above mentioned buffers in different tubes. This was done by removing the supernatant from the stock solution and resuspending the beads with each buffer. All the samples were further sonicated in an ultra-sonicator to avoid any pre-clumping of the magnetic beads. 1 µl of 1.5 cSt silicone oil was pipetted on a Teflon coated glass slide and 1 µl of the beads were pipetted on the oil droplet and a sandwich is created by placing a cover slip over the bead droplet. The gap height used in the sandwich was 200 µm. A 0.5 Tesla magnet was placed at a distance of 5 mm from the bead droplet on the cover slip. The attraction of the beads was observed under a microscope and periodic images were taken.

Figure 11:
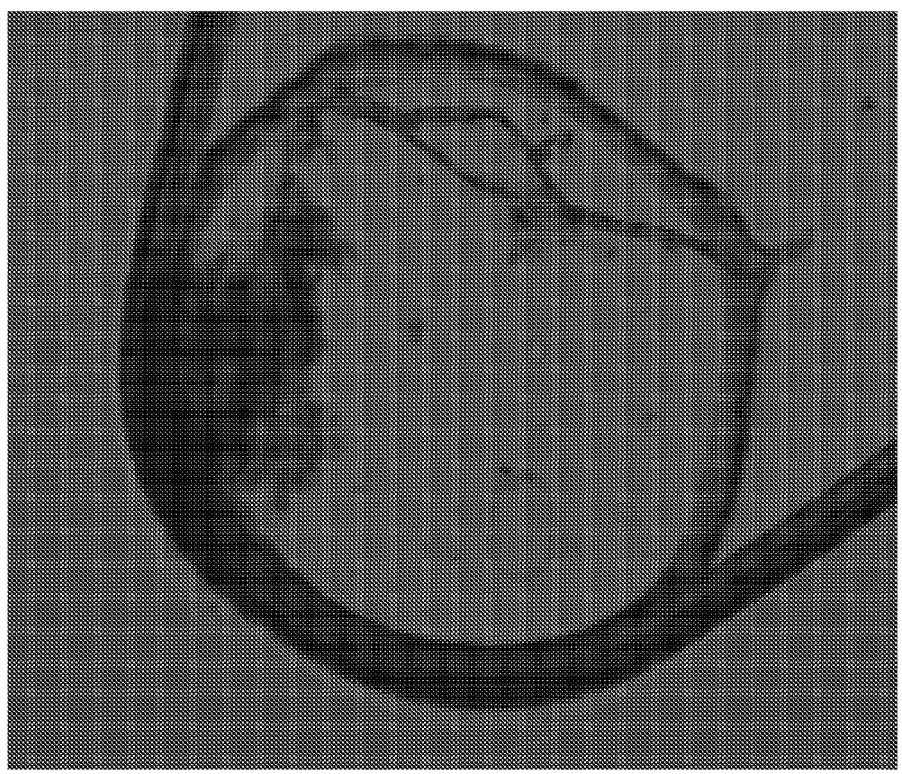
FIG. 11 is an illustration of BioMAG streptavidin beads with no surfactant in the supernatant.
Figure 12:
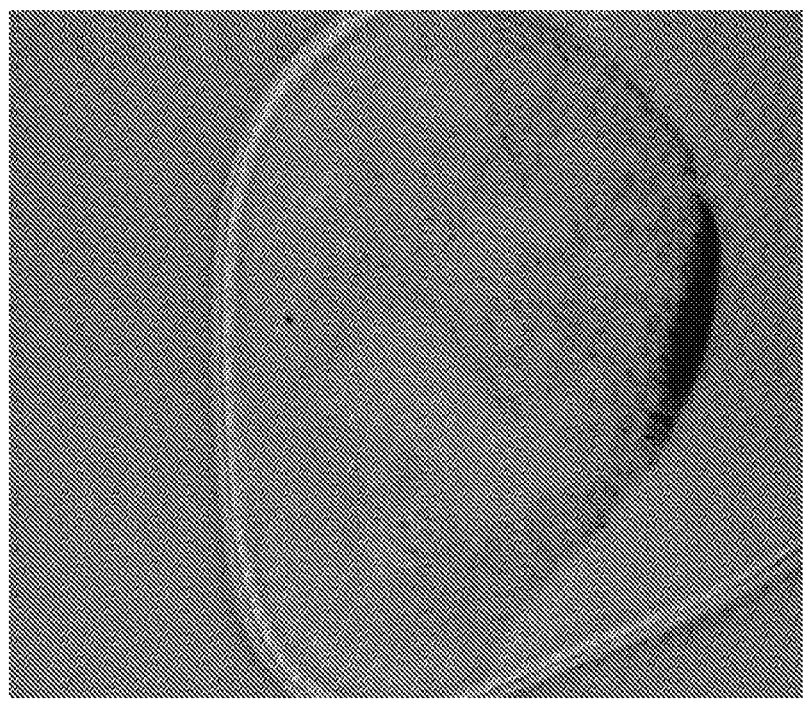
FIG. 12 is an illustration of BioMAG streptavidin beads with 0.005% Tween® 20 in PBS.
Figure 13:
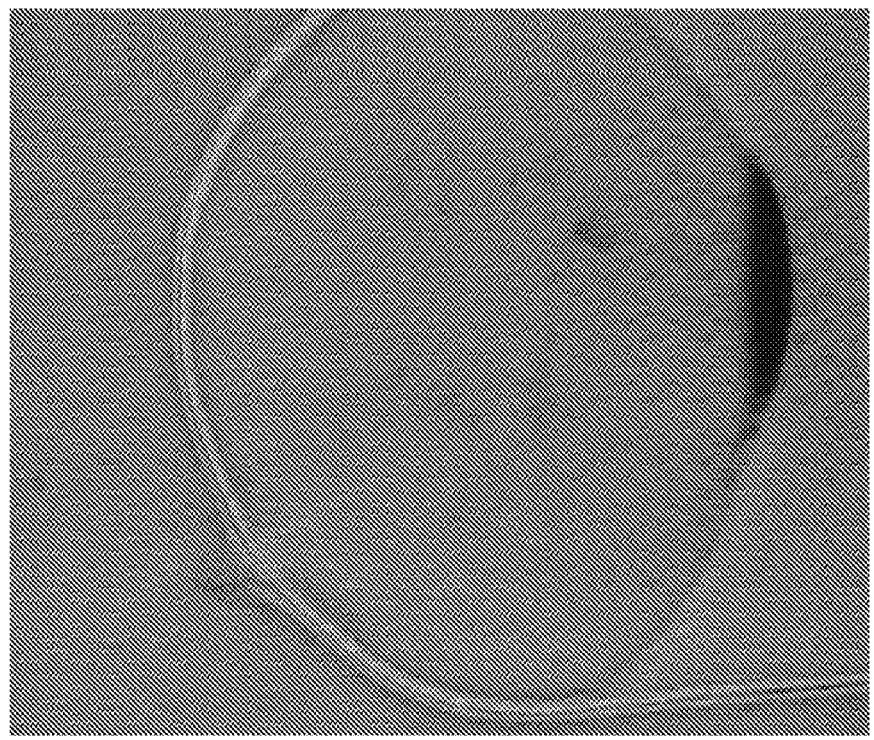
FIG. 13 is an illustration of BioMAG streptavidin beads with 0.01% Tween® 20 in PBS.

Observations—It was observed that the beads got attracted well with less aggregation/clumping in the presence of a surfactant (Tween® 20) in the buffer. In all the other cases, either the attraction was poor or there was significant aggregation/clumping of the beads as seen in FIGS. 11 and 12. The concentration of the surfactant in the buffer also affects the attraction of the magnetically responsive beads. It was found out that a 0.01% of Tween® 20 (FIG. 13) was good for efficient attraction with least clumping. The same experiments were performed with Dynal® MyOne™ Streptavidin coated beads and similar observations were made.

8.7.2 Magnetic Field Strength

One of the most important parameters that would affect the efficiency of attraction with very less aggregation is the magnetic field strength that is applied to the magnetically responsive beads.

Materials—BioMag streptavidin beads suspended in 0.01% Tween® 20, Dynal® Myone™ streptavidin beads suspended in 0.01% Tween® 20, 0.5 Tesla Neodymium magnets (ND 42) with pull forces 5 lbs and 1.25 lbs, 1 Tesla Neodymium magnets with a pull force of 1.25 lbs obtained from K & J. Magnetics.

Experimental setup—BioMag streptavidin beads were diluted 4 times and suspended in 0.01% Tween® 20 and a 1 µl droplet was sandwiched between Teflon coated microscope slide and Teflon coated cover slip with 1.5 cSt silicone oil as the filler fluid. The gap height of the sandwich used was 200 µm. A 0.5 Tesla Neodymium (ND 42) magnet with a pull force of 5 lbs was placed at a distance of 5 mm from the bead droplet on the cover slip and periodic images were taken using a microscope. Same experiment was repeated with a 0.5 Tesla magnet with a lesser pull force (1.25 lbs) and a 1 Tesla magnet with a pull force of (1.25 lbs)

Figure 14:
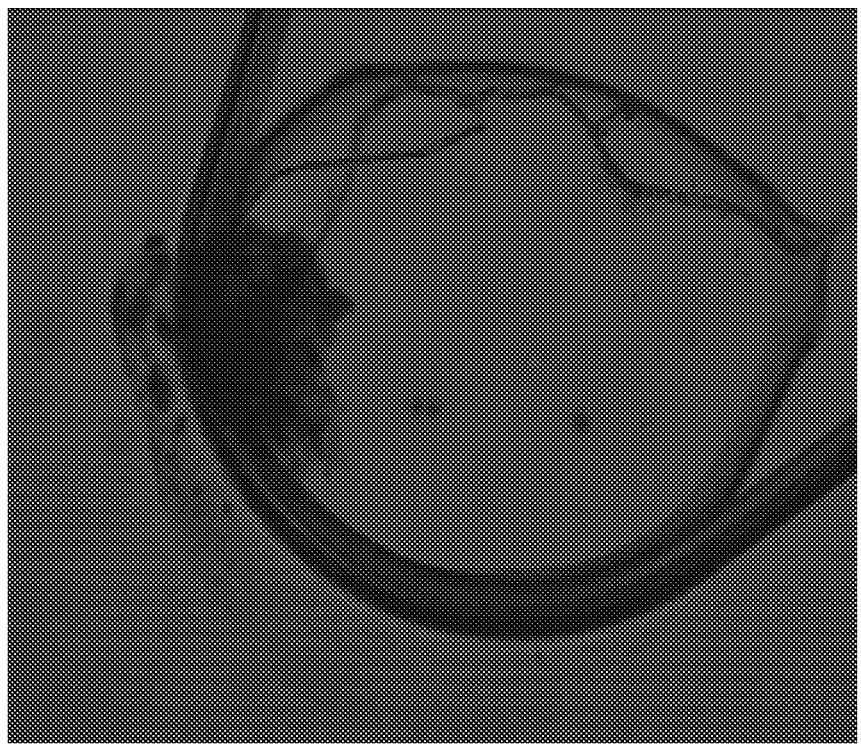
FIG. 14 is an illustration of BioMAG streptavidin beads in 0.01% Tween® 20 attracted with a 0.5 Tesla magnet (5 lbs pull force)
Figure 15:
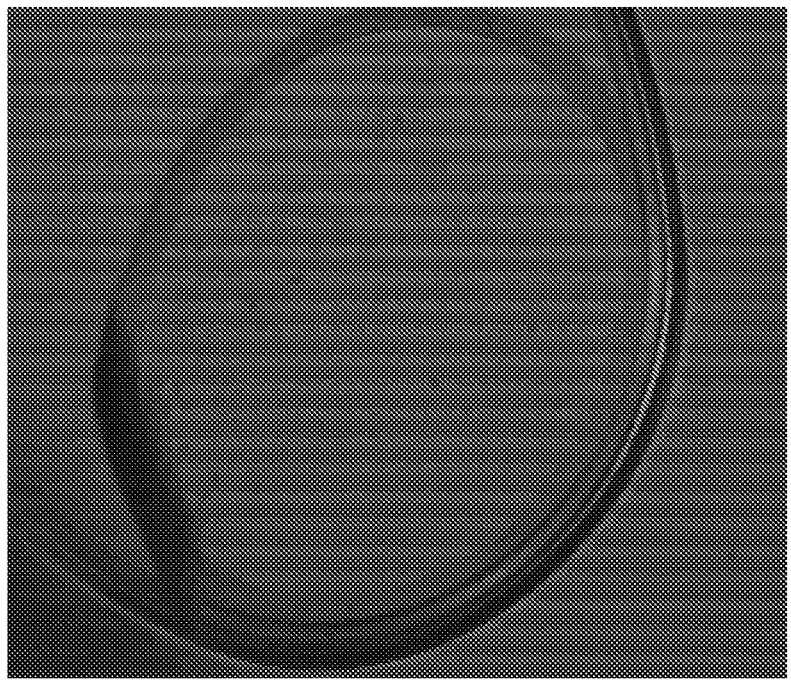
FIG. 15 is an illustration of BioMAG streptavidin beads in 0.01% Tween® 20 attracted with a 0.5 Tesla magnet (1.25 lbs pull force)

Observations—It was observed that a magnet with a higher pull force (5 lbs) resulted in aggregation of the beads and also adsorption to the surface of the top plate and the microscope slide (FIG. 14). The 0.5 Tesla magnet with 1.25 lbs pull force provided efficient attraction, but the attraction was not reproducible. However the attraction was consistent with minimal aggregation with a 1 Tesla magnet with 1.25 lbs pull force (FIG. 15). Hence the magnetic strength/pull force of the magnet has to be optimized such that (1) it is sufficiently strong to immobilize the magnetic beads (2) it is so strong that the beads form aggregates/clumps (3) it is not so strong that the resuspension occurs poorly when the magnetic field is removed.

8.7.3 Concentration of the Bead Suspension

The solid content in the stock solution of the bead suspension is around 2-3%. The concentration of the beads in a particular volume of the buffer is an important factor to achieve high bead attraction efficiency. However the concentration varies with the size of the unit droplet and the gap height used.

Materials—BioMag Streptavidin beads suspended in 0.01% Tween® 20

Experimental setup—The BioMag Streptavidin beads from the stock solution were diluted 2, 4 and 6 times suspended in 0.01% Tween 20. A 1 µl droplet of the beads was sandwiched between a Teflon coated microscope slide and a cover slip with a gap height of 200 µm. The beads were attracted using a 1 Tesla magnet with a pull force of 1.25 lbs at a distance of 5 mm from the droplet. The experiment is repeated with different concentrations of the beads and periodic images were taken using a microscope.

Figure 16:
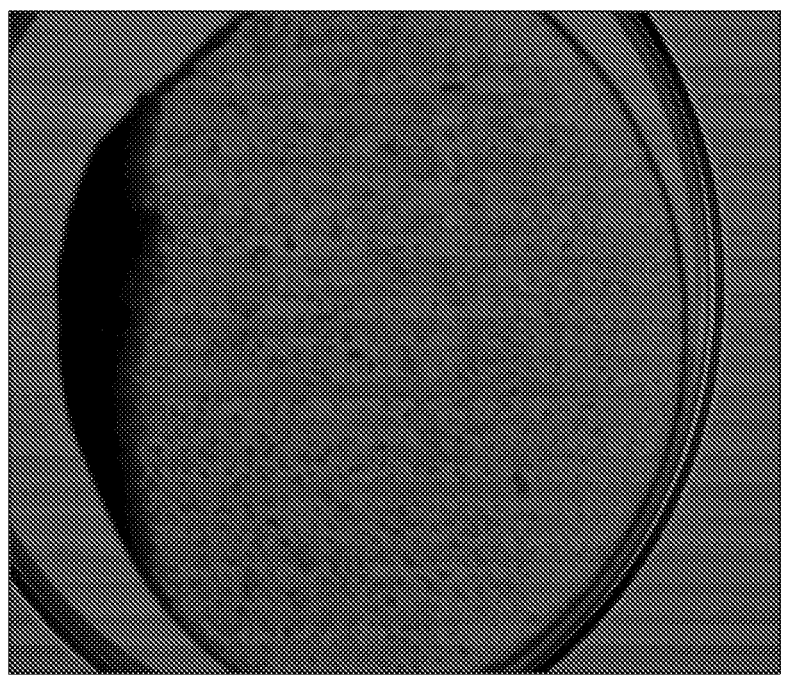
FIG. 16 is an illustration of BioMAG streptavidin beads (undiluted stock) in 0.01% Tween® 20.
Figure 17:
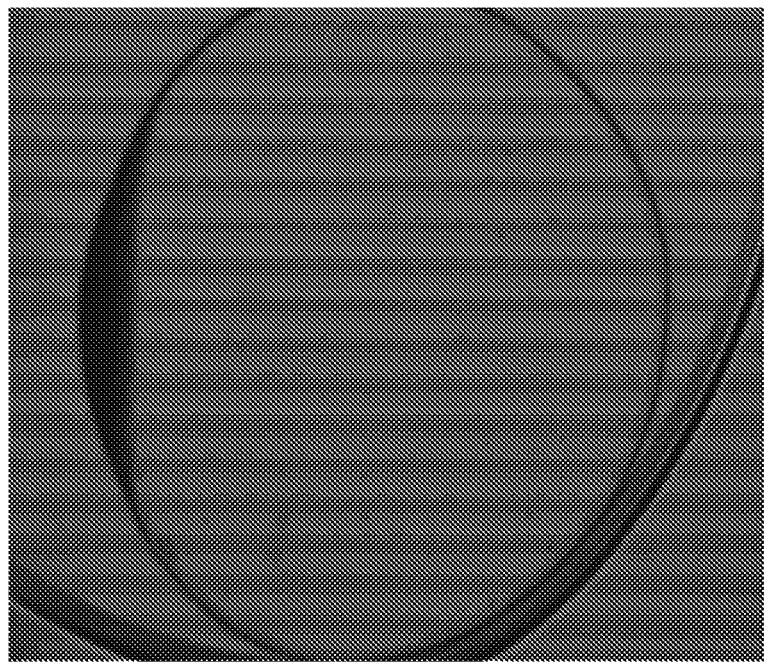
FIG. 17 is an illustration of BioMAG streptavidin beads (4 times diluted) in 0.01% Tween® 20.
Figure 18:
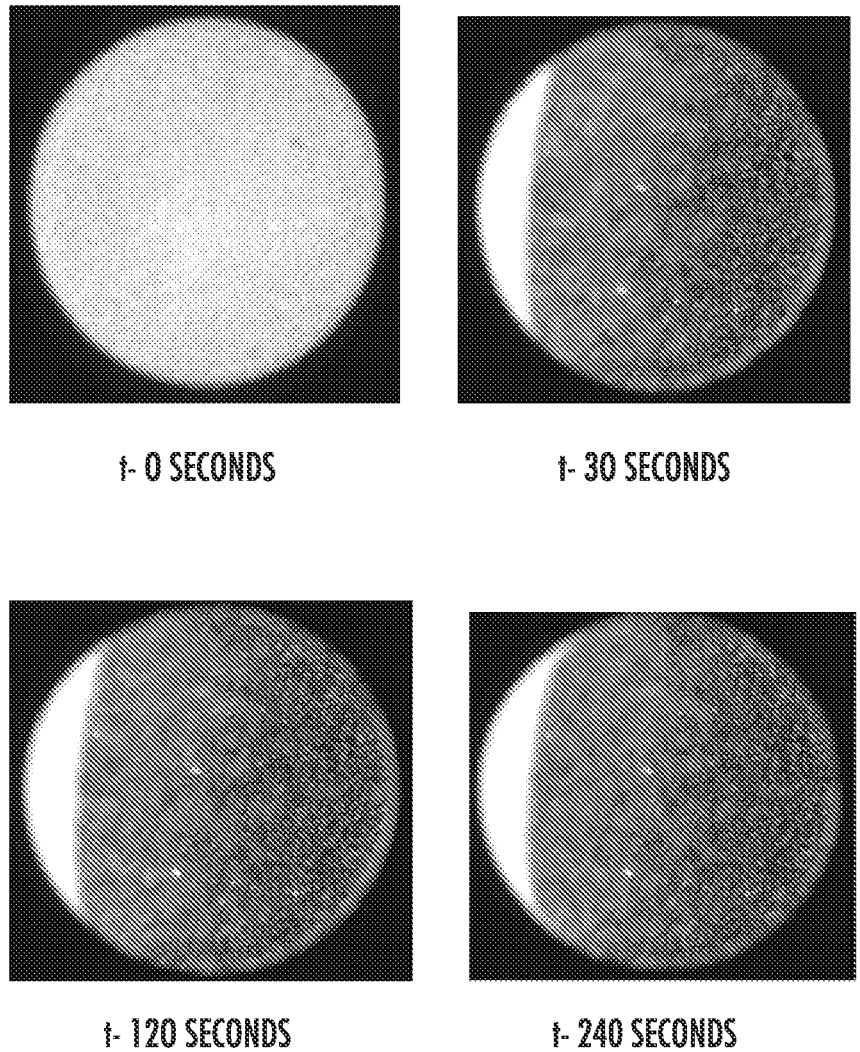
FIG. 18 is an illustration depicting the attraction of fluorescin labeled magnetic beads.

Observations—It was observed that there was huge congestion and the attraction was very poor for the highly concentrated beads (FIG. 16) when compared to the 4 times diluted bead droplet (FIG. 17). However the optimum concentration of the beads depends on the solid content of the bead suspension and varies from stock to stock.

It can be seen from the above figures that the concentration of the beads affects the efficiency of attraction. However the optimum concentration depends on the gap height used and the droplet size and varies with the electrode design.

8.7.4 Position of the Magnet

The position of the magnet has a huge influence on the bead attraction while performing electrowetting operations to hold the beads and remove the excess supernatant. The process of washing the magnetic beads basically involves repetition of the bead droplet merging with a wash buffer solution, splitting and removal of the excess supernatant and resuspension of the beads until acceptable levels of washing are achieved. To achieve efficient washing the magnet should be positioned strategically which would allow immobilization of the beads at a point and remove the excess supernatant with minimal loss of beads. Hence the magnetic field lines were simulated using Maxwell software by Ansoft with the 1 Tesla neodymium magnets placed at different positions as described below.

Figure 19:
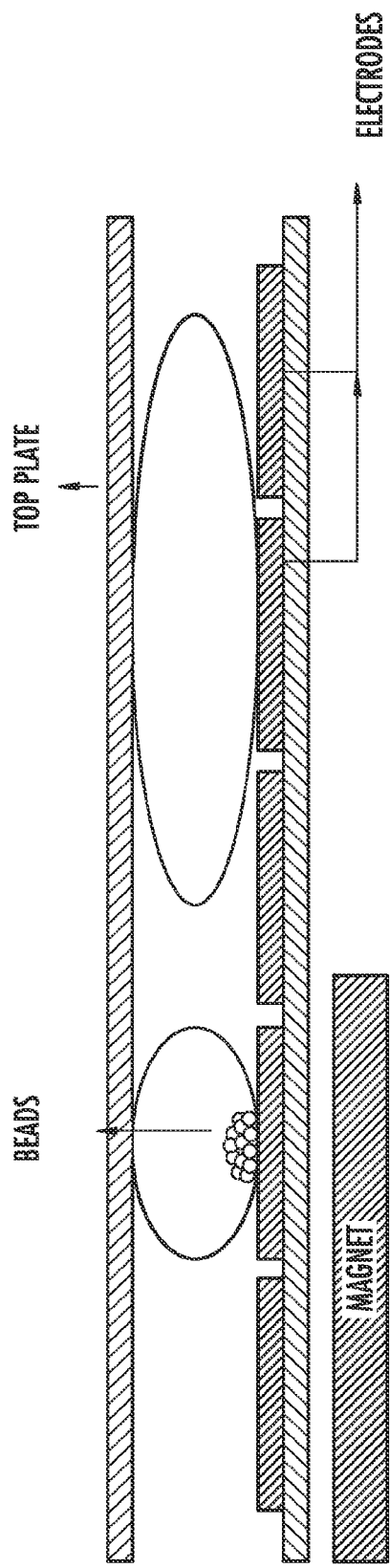
FIG. 19 is a side view illustration of a Tesla magnet placed underneath an electrode with a bead droplet.
Figure 20:
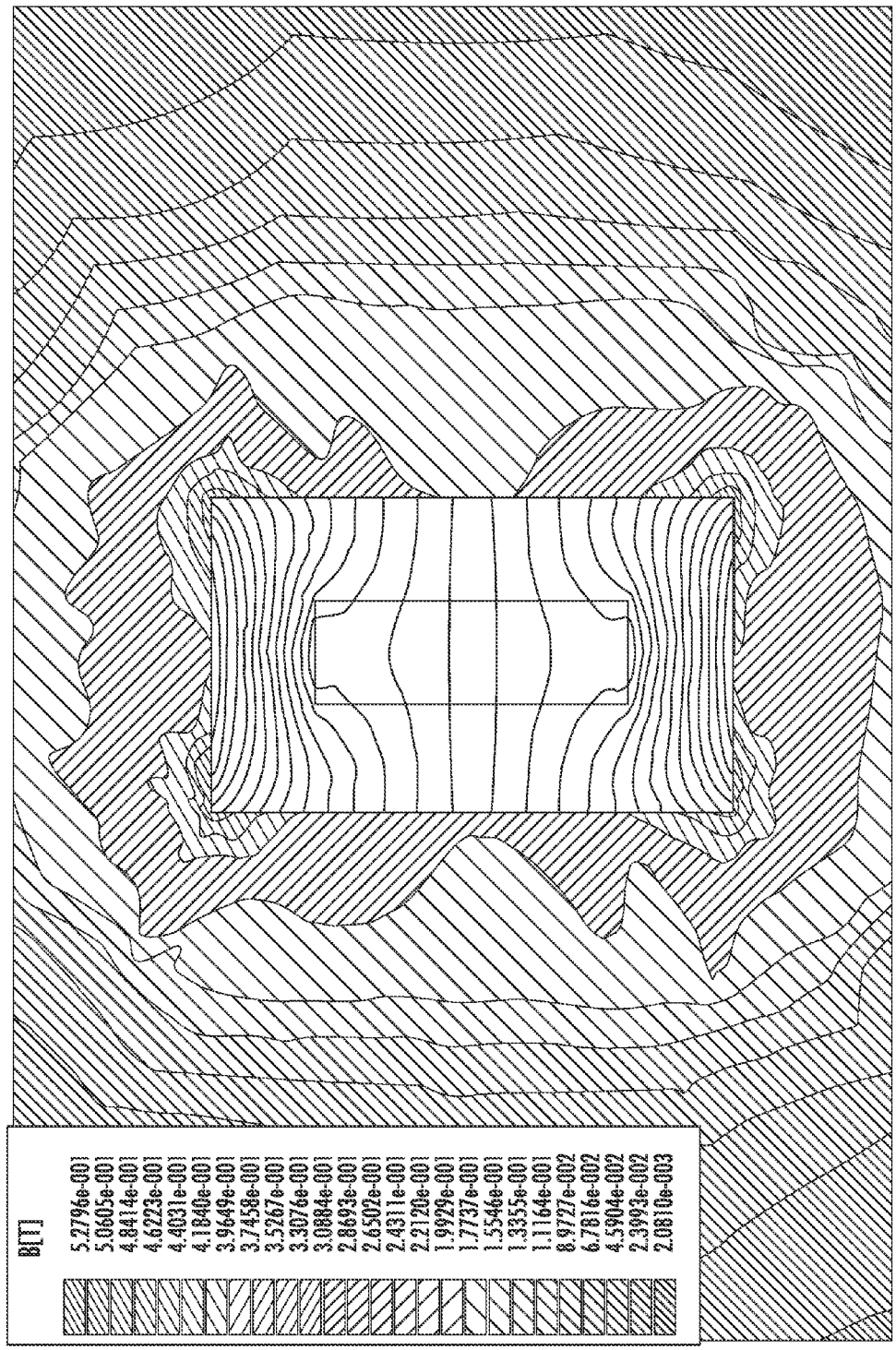
FIG. 20 is an illustration of a simulation of a 1 Tesla magnet placed under a bead droplet.

Configuration 1—FIG. 19 shows a side view of the bead droplet sandwiched between the chip with electrodes and a top plate with a spacing filled with filler 1.5 cSt Silicone oil which is the filler fluid (not shown). This position of the magnet described in FIG. 19 was simulated using Maxwell software such that the "N" pole of the magnet is exactly underneath the bead droplet. The simulation (FIG. 20 shows a top view of the electrode (small red rectangle) and the magnet underneath (large green rectangle) with the flow happening from the top of the rectangle (start) to the bottom (splitting). The magnet is bigger than the electrode on the chip and hence it covers more than one electrode. It can be seen from the simulation that high surface field lines pass exactly through the center of the electrode and gets weaker at the bottom which is the splitting zone to remove the excess supernatant from the beads.

Figure 21:
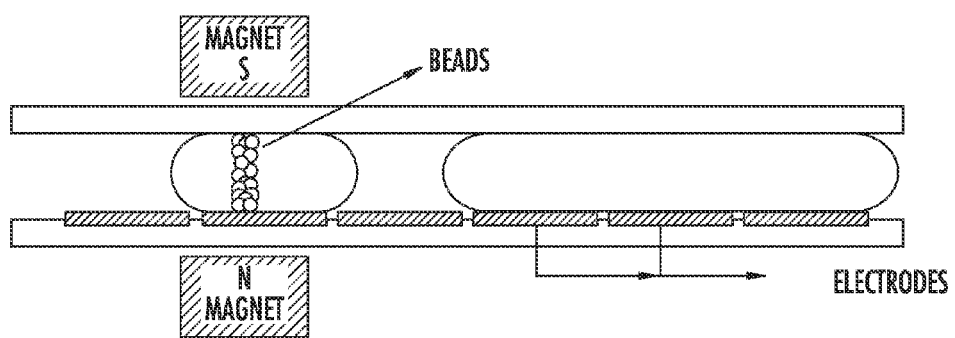
FIG. 21 is a side view illustration of Tesla magnets placed underneath and over bead droplets with the opposite poles of the magnets facing each other.
Figure 22:
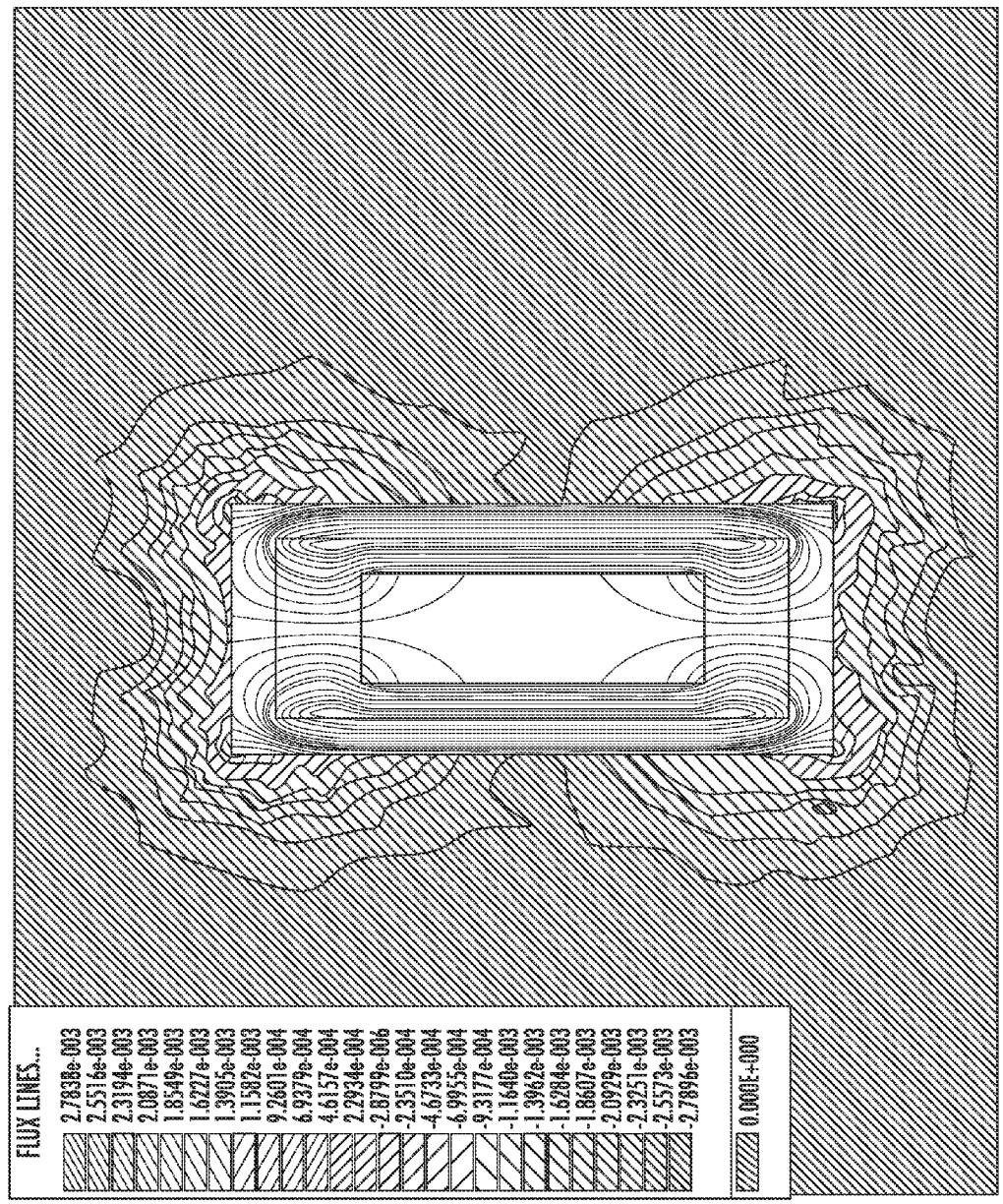
FIG. 22 is an illustration of a simulation of a 1 Tesla magnet placed underneath and over a bead droplet.

Configuration 2—In another configuration that is optimized for efficiently washing the magnetic beads, the 1 Tesla magnets were arranged such that the opposite poles of both the magnets face each other as depicted in the FIG. 21. Magnets are positioned relative to one or more transport electrodes in order to optimize the path of the magnetic field lines through the liquid within the droplet. The simulation in FIG. 22 shows a top view of the magnets (large green rectangles) and the electrode (small red rectangle). The software doesn't allow overlapping of the magnets; hence they were placed such that there is no overlap. It was observed that the magnetic field lines pass through the edges of the electrodes from the north pole of the magnet underneath to the south pole of the magnet over the electrode. This would form a pillar of the beads as shown in FIG. 21 which would enable lesser force for the splitting of the supernatant.

Figure 23:
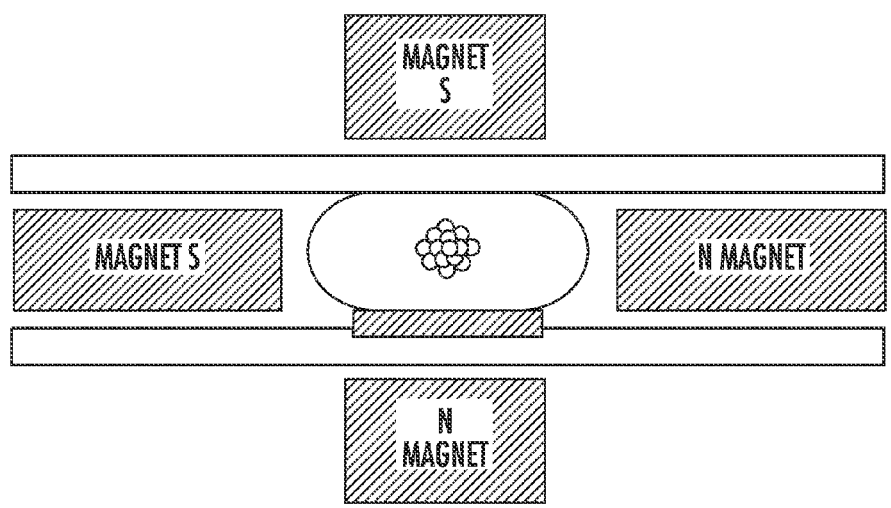
FIG. 23 is a side view illustration of Tesla magnets placed on four sides of a droplet.
Figure 24:
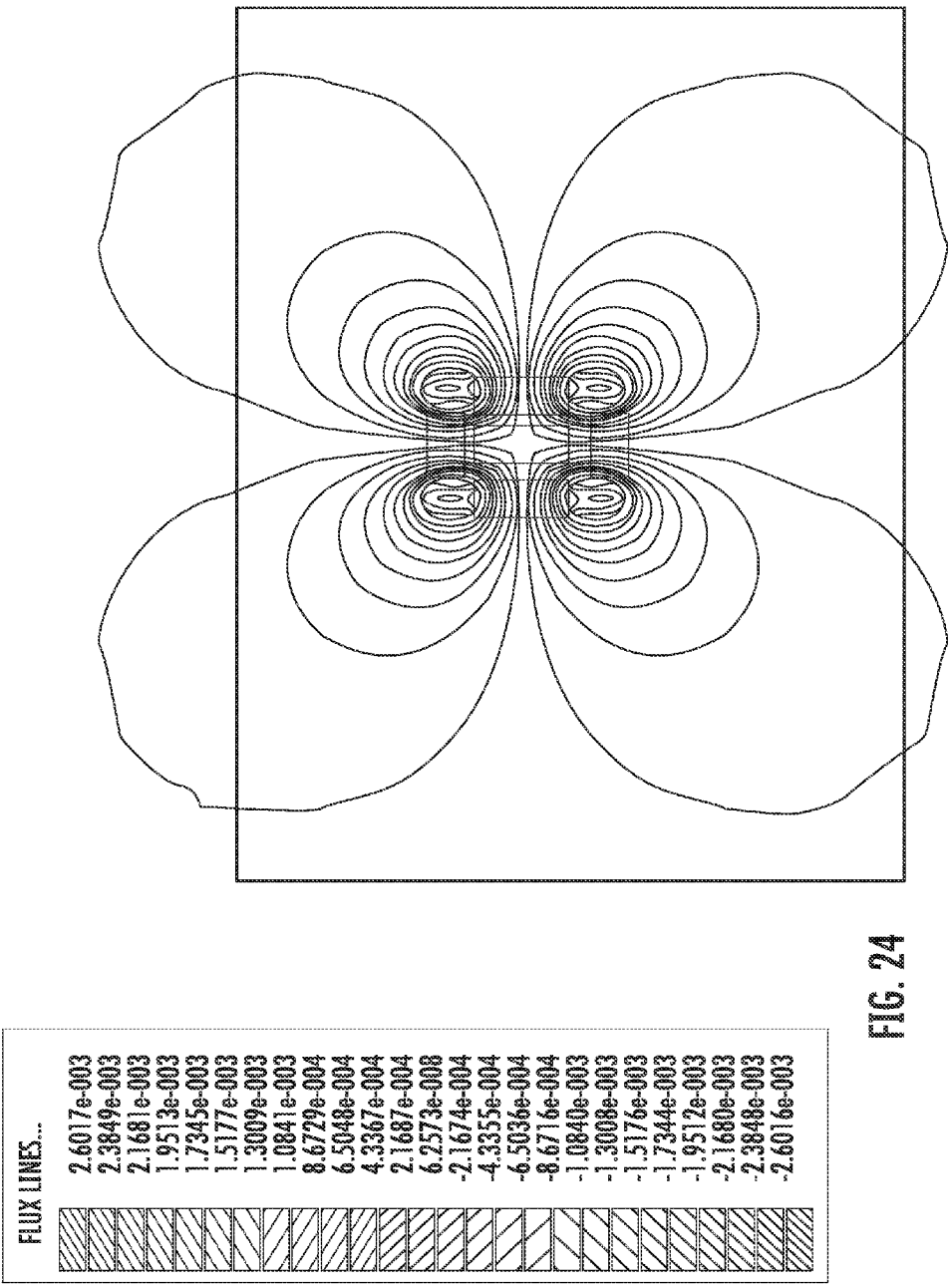
FIG. 24 is an illustration of a simulation of the magnetic filed lines in a quadrapole arrangement.

Configuration 3—In another configuration optimized to efficiently wash the magnetic beads the magnets were arranged on the top and bottom of the bead droplet with the opposite poles of the magnet facing each other and also magnets on either side of the droplet with the poles facing each other as shown in FIG. 23. This ensures that the magnetic field lines pass exactly through the droplet of beads which would retain them in the place. The simulation (FIG. 24) was done in Maxwell software and it was observed that the magnetic field lines were such that the beads will be retained exactly at the center of the droplet.

This ensures less force required for the splitting process to remove the excess supernatant. This type of configuration is typically called quadrapole magnet arrangement. A part from the above mentioned magnet configurations, magnets can be placed in any arrangement which can efficiently retain the beads in the droplet and ensure efficient splitting of the supernatant. It should be mentioned that the splitting and the bead retention should be reproducible because washing is a redundant process until required wash levels are achieved. In all the configurations described above the magnets can either be permanent neodymium magnets or electromagnets. Permanent Neodymium magnets (ND 40 and ND 42) with surface field of 1 Tesla and 1.25 Tesla were used for this research. The magnet configuration shown in FIG. 19 with a magnet right underneath the electrode has been used in this research because in all the other configurations, visualization would be a problem with the magnets blocking the scope. Hence a 1 Tesla neodymium magnet (ND 42) was used for this research placed right underneath the electrode with the bead droplet.

The size of the ND 40 magnet used in this research was 0.2"×0.1"×0.048" which would span at least three electrodes each spanning 1250 µm×1250 µm. Having magnetically responsive beads retained at a centralized location within the droplet, the splitting operation should occur such that the splitting zone is outside the surface field of the magnet(s). Experiments were performed with the splitting zone within in the magnetic field and outside the magnetic field.

Materials—Dynal® Myone™ Streptavidin coated beads (1.05 µm diameter), 0.01% Tween® 20 in PBS, Parylene and 1% Teflon coated glass chip with 1250 µm×1250 µm chrome electrodes, 1% Teflon coated Indium Tin oxide (ITO) glass plate used as a top plate for grounding the droplet.

Figure 25:
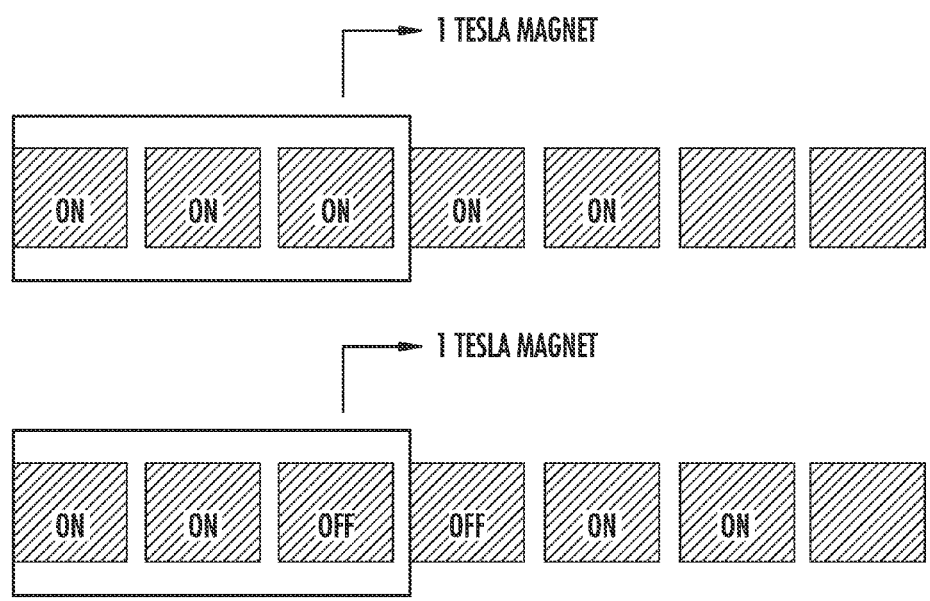
FIG. 25 is a schematic illustration of a splitting mechanism to retain beads and remove supernatant.
Figure 26:
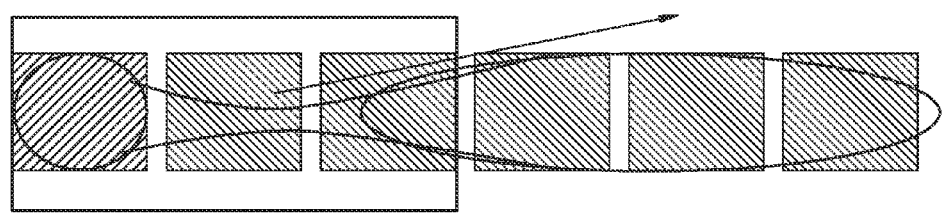
FIG. 26 is a schematic illustration of splitting of supernatant retaining beads.

Experimental setup—A 1 µl of the Dynal streptavidin coated magnetically responsive beads diluted 5 times from the stock solution was pipetted on an electrode and sandwiched with the Teflon coated ITO top plate with the filler fluid being 1.5 cSt silicone oil. The gap height in this case was 300 µm. 4 µl of 0.01% Tween® 20 was added to the beads and from the side of the top plate and allowed to settle for the beads to get attracted. The splitting mechanism was done as shown in the FIGS. 25 and 26. The electrodes adjacent to the one with the beads were switched on to form a slug of liquid in the first stage. The electrodes at the end of the magnet where the surface field lines are weak were switched off for the split to occur at that point. This retains the beads within the droplet and also removes most of the excess supernatant.

Figure 27:
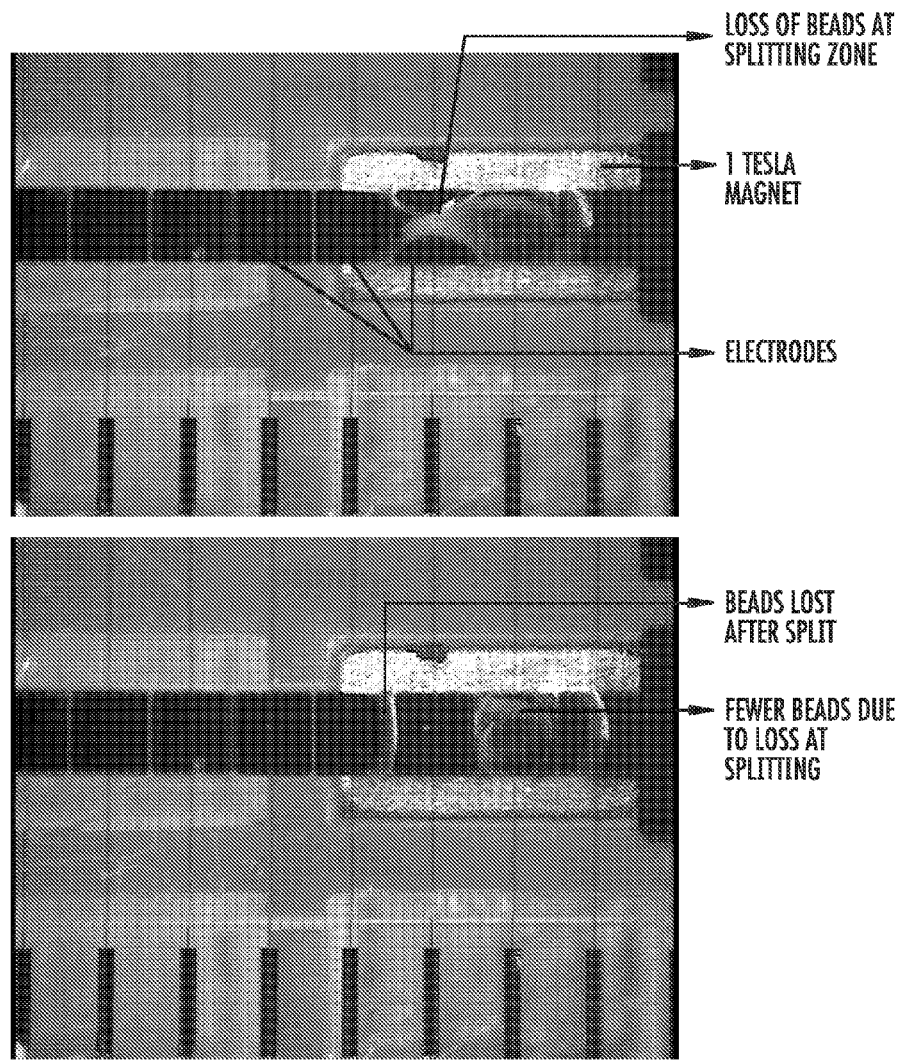
FIG. 27 is an illustration depicting the loss of beads with the splitting within the magnetic field.
Figure 28:
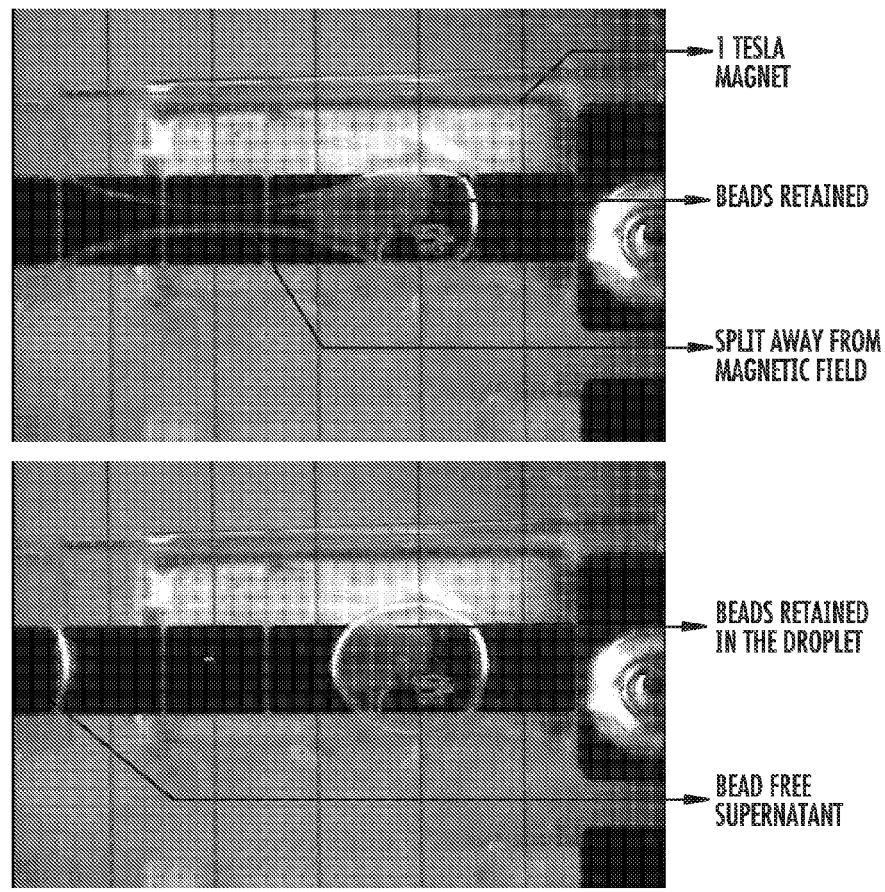
FIG. 28 is an illustration depicting splitting away from the affect of magnetic field.

Observations—FIG. 28 depicts the retention of the beads and splitting of the droplet. However if the splitting happens within the zone where the magnetic field is strong enough there would be loss of beads which in turn would diminish the signal. FIG. 27 shows the loss of beads into the supernatant when the splitting happens within the affect of the magnetic field. However when the droplet was split away from the magnetic field all the beads were retained within the droplet which is shown in the FIG. 28.

8.8 Washing of the Magnetic Beads

Washing of magnetic beads in an immunoassay involves repetitive droplet merging (with a wash buffer solution), bead immobilization, splitting of the supernatant and bead resuspension operations until acceptable levels of washing is achieved. Among the above mentioned operations the bead retention and dilution efficiency are considered the most important operations to achieve the acceptable wash efficiency retaining all or most of the beads. Hence separate experiments were designed and performed to quantify the bead retention and the dilution efficiency on chip.

8.8.1 Bead Retention

Materials—Dynal® Myone™ Streptavidin coated magnetic beads (1.05 µm diameter), Biotinylated Horse radish peroxidase (HRP) obtained from EY laboratories, 0.01% Tween® 20, Lumigen Ultra PS-Atto solutions A and B from Lumigen inc., Parylene and 1% Teflon coated glass chip with 1250 µm×1250 µm chrome electrodes, 1% Teflon coated Indium Tin oxide (ITO) glass plate used as a top plate for grounding the droplet.

Experimental setup and Methods—Dynal® Myone™ streptavidin coated magnetic beads were labeled with HRP enzyme by reaction of the beads with the biotinylated HRP. The stock concentration of the magnetic beads was 10 mg/mL which can bind 20-25 µg of biotinylated IgG. The stock concentration of the beads was diluted 5 times to enable minimal loss of the beads at the splitting zone due to excess number of beads per unit volume. 1 µl of the bead solution was added to 10 µl of 0.1 mg/ml of biotinylated HRP and allowed to incubate for 30 minutes. The biotin on the HRP would react with the streptavidin on the magnetic beads to form a strong bond ($K=10^{15}$ M) labeling the magnetic beads with HRP. 1 µl of these HRP labeled beads were pipetted on an electrode and was sandwiched using Teflon coated ITO top plate. The gap height used was 300 µm and was filled 1.5 cSt Silicone oil. A 1 Tesla neodymium magnet placed underneath the bead droplet and washing was done by adding 4 µl of 0.01% Tween 20 for each wash as described in the above section. This process was repeated 5 times and the supernatant was collected each time. The supernatant should not have any beads lost because of the optimized position of the magnet and the splitting zone. However in order to quantify the loss of beads the supernatant was assayed in a Costar opaque 96 well plate. The supernatant was collected from the chip and transferred into one of the wells in the plate. 5 µl of the magnetic beads labeled with HRP was pipetted into another well and 5 µl of the Tween® 20 used for washing the bead was pipetted into another well of the 96 well plate. The substrate was prepared by mixing equal volumes of Lumigen Ultra PS Atto solution A and solution B and 50 µl of the substrate was added to each well and the chemiluminescence was read using a BioTek plate reader for 8 minutes and the reading taken every 20 seconds at a gain of 80. The mean velocity of the reaction was calculated by taking the slope of the first five points for all the wells.

Results—Since the HRP concentration on the magnetic beads is very high, the chemiluminescence obtained from the well with 5 µl of the magnetic beads is really high and turned out to be a flash which was missed because of the delay in addition of the substrate and transferring it to the plate reader. Hence only the reduction in the chemiluminescence was read by the plate reader which gave a negative slope.

Mean $V$ obtained for the HRP labeled beads (positive control)=−1.9289 E 6 mLum/min Mean $V$ obtained for Tween 20 (negative control)=900 mLum/min Mean $V$ obtained for the supernatant (data)=1350 mLum/min However the quantification of the concentration of beads that were lost during the wash step can be done using a standard curve between chemiluminescence values (mean V) and different concentrations of HRP labeled beads.

Figure 29:
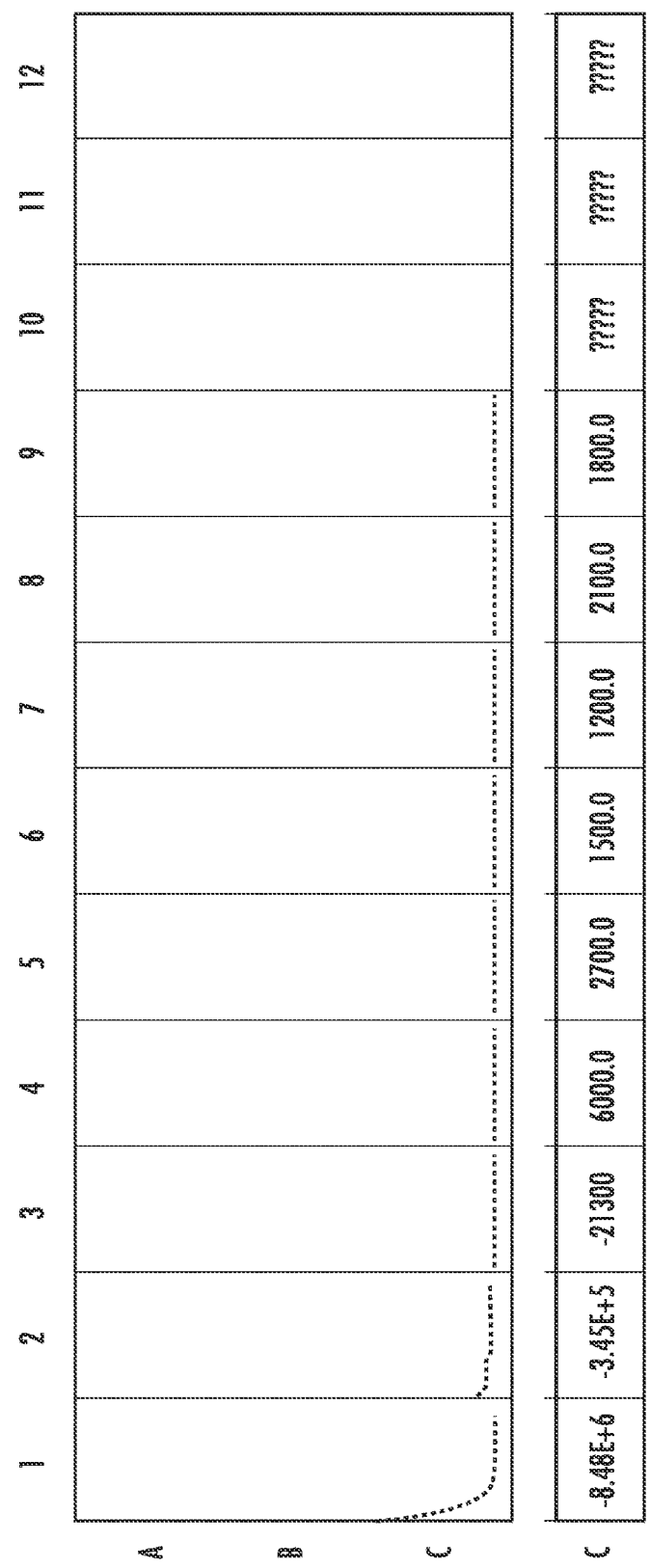
FIG. 29 is a graphical illustration depicting the kinetic curves, mean V values for each concentration of HRP labeled magnetic beads.
Figure 30:
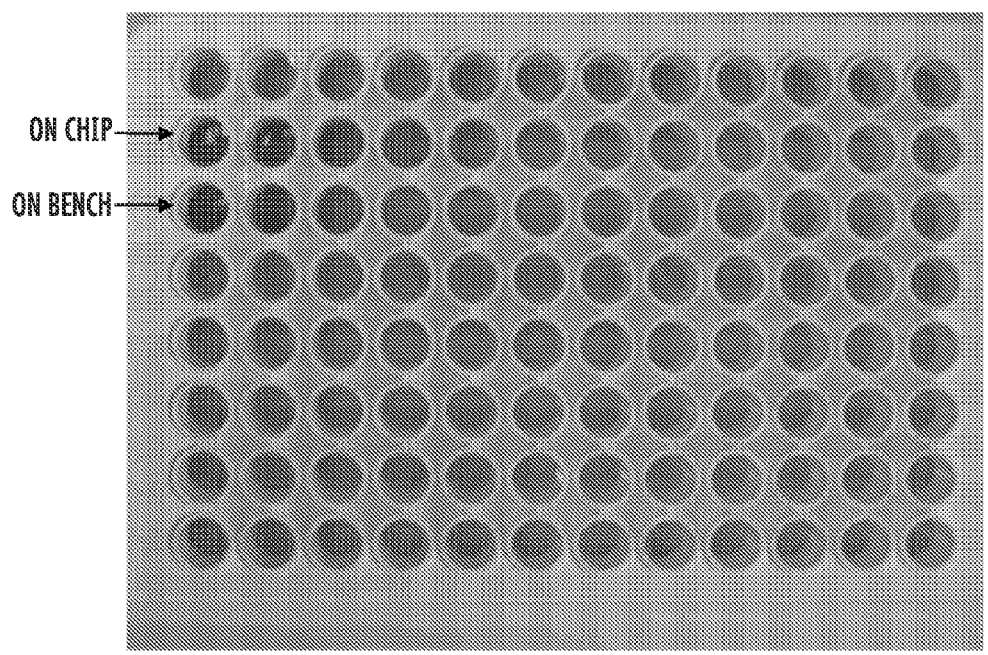
FIG. 30 is an illustration of a 96 well plate comparing the washes on bench and chip.

Standard curve for HRP labeled magnetic beads—2 mg/ml of the HRP labeled beads were diluted serially with Tween® 20 until 2E−9 mg/ml and 5 µl of each concentration of the beads were transferred into a well of a 96 well Costar opaque plate. 50 µl of the Lumigen Ultra PS atto substrate was added and the chemiluminescence read for 8 minutes every 20 seconds. FIG. 29 depicts the kinetic curves, mean V values for each concentration of the HRP labeled magnetic beads.

| Quantification of beads lost during the washing process- | |
| --- | --- |
| Mean V value for the supernatant = | 1350 mLum/min |
| Concentration range of the beads for the above mean V value = | 2 E–7 to 2 E–6 mg/mL |
| No. of beads per mg of beads (stock solution) = | 7 – 12 × 10^9 beads |
| No. of beads lost = | 5 E–3 mL × 2 E–7 mg/mL |
| = | 1 E–9 mg = 1 E–9 × 12 E9 |
| = | 12 beads |
| Initial no. of beads in the 1 µl droplet = | 25 E+6 beads |
| Bead retention efficiency = | {1 – [12/25 E6]} × 100 |
| = | 99.99995% |

Observation—Hence with the depicted magnet configuration and the splitting protocol almost all the beads are retained within the droplet and remove the excess supernatant.

8.8.2 Dilution Efficiency

One of the other important operations to achieve good wash efficiency apart from good bead retention is the dilution efficiency after every wash. An experiment was designed to compare the wash dilution efficiency done on chip and bench.

Materials—Dynal® Myone™ Streptavidin coated magnetic beads, Horseradish peroxidase enzyme, 0.01% Tween® 20, Parylene and 1% Teflon coated glass chip with 1250 µm×1250 µm chrome electrodes, 1% Teflon coated Indium Tin oxide (ITO) glass plate used as a top plate for grounding the droplet, Amplex red substrate for HRP enzyme.

Methods—Dynal streptavidin coated magnetic beads (1.05 µm diameter) were diluted 5 times and suspended in 10 µg/ml of HRP enzyme prepared in 0.01% Tween20. 1 µl of these HRP suspended streptavidin coated magnetic beads were pipetted on an electrode and sandwiched using an ITO top plate and the spacing is filled with 1.5 cSt silicone oil. The gap height used was 300 µm. The magnet configuration used for the bead retention experiments was used here. The bead droplet was washed with 4 µl samples of 0.01% Tween 20 and the supernatant was collected after every wash and transferred to a well in a 96 well transparent plate. The same experiment was performed even on bench with the washing done with 96 well magnet holder and a pipette to remove the supernatant. Amplex red substrate was added to each and every well which had the supernatant after each wash from the bench and the chip. The absorbance was read at a wavelength of 570 nm using the Biotek plate reader for 8 minutes. The mean velocity was obtained by calculating the slope considering the initial 10 points.

Figure 31:
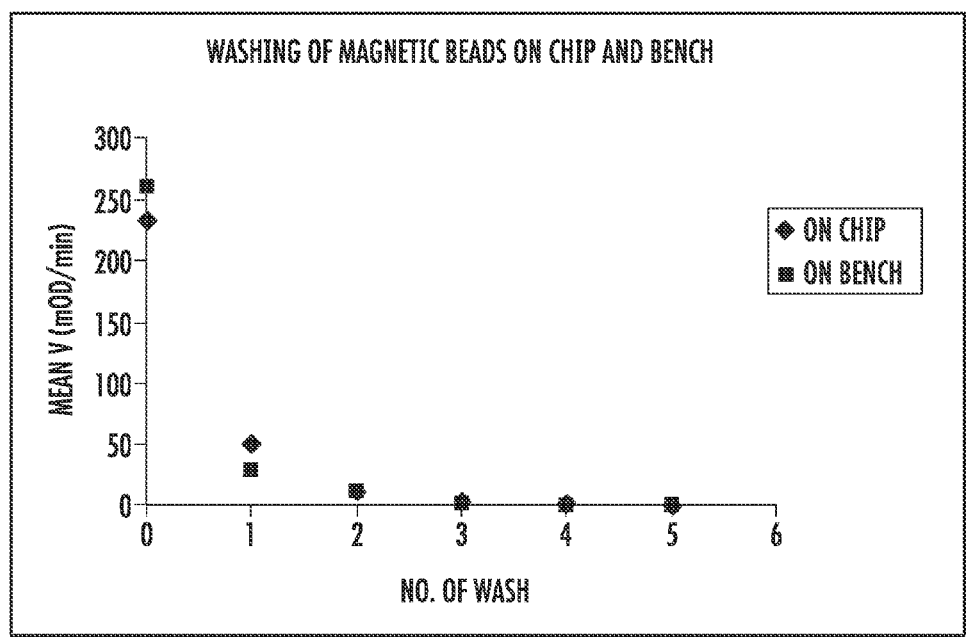
FIG. 31 is a graphical illustration depicting the comparison of washing on chip and bench.
Figure 32:
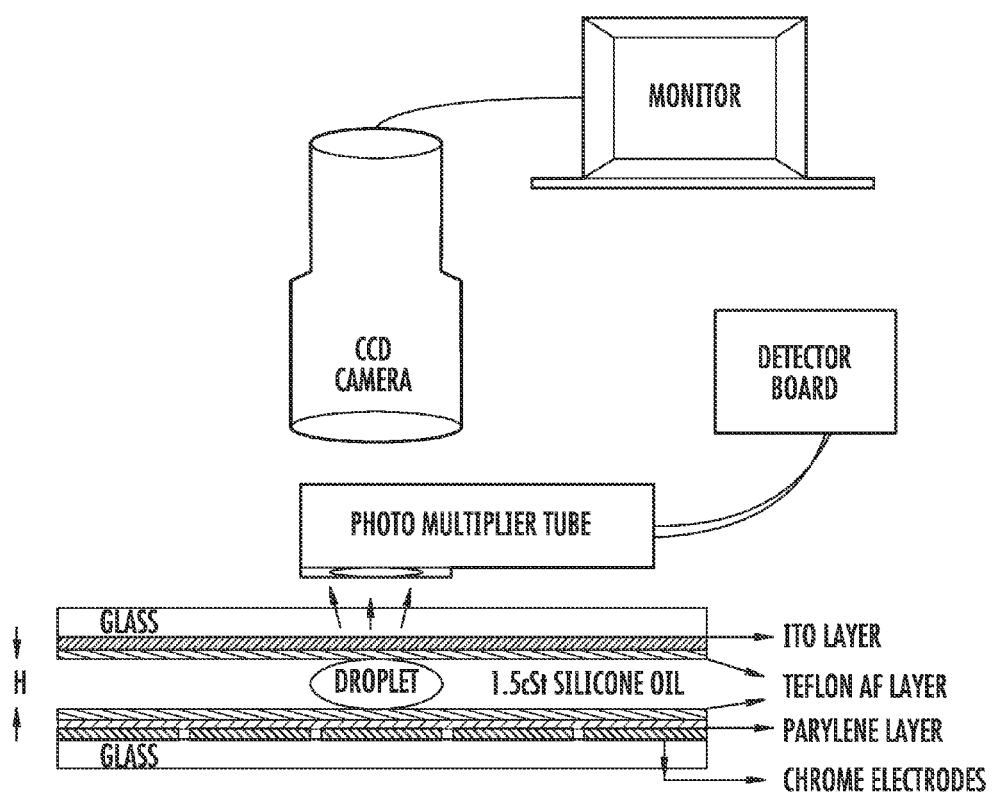
FIG. 32 is an illustration of a chemiluminescence detection setup.

Results—It was observed that the washing on the chip and bench followed a similar trend with the supernatant (HRP enzyme) getting diluted after each wash until the background absorbance was obtained (FIGS. 31 and 32).

The above experiment was done with different starting concentrations of HRP and different number of wash steps was required to get the background absorbance values. Moreover it also matched with the data obtained from the bench very well. Hence the washing of the magnetically responsive beads was demonstrated on chip using a 1 Tesla magnet right underneath the bead droplet with splitting of the supernatant occurring away from the magnetic field.

8.9 Magnetic Immunoassay on Chip

Washing of magnetically responsive beads which is the most important step to perform the magnetic immunoassay on chip was described in the previous section. The magnetic immunoassay was performed on chip considering all the parameters described above. The analyte chosen to perform the magnetic immunoassay was insulin. The rationale behind choosing insulin as the analyte is the prevalence of diabetes caused either due to excess or lack of insulin in the blood.

8.9.1 Experimental Setup

Materials—Anti Insulin antibody labeled with magnetic beads which acts as the primary antibody with the solid phase, anti insulin antibody labeled with alkaline phosphatase (ALP) enzyme which acts as the secondary antibody, block IgG for blocking secondary reactions, all obtained from a kit for performing the magnetic immunoassay in Access® 2 Immunoassay system by Beckman coulter Inc., insulin samples, Lumigen APS-5 substrate (chemiluminescence substrate for ALP from Lumigen Inc.), 1.5 cSt silicone oil, Access® wash buffer, Parylene and 1% Teflon coated glass chip with 1250 µm×1250 µm chrome electrodes, 1% Teflon coated Indium Tin oxide (ITO) glass plate used as a top plate for grounding the droplet.

8.9.2 Chemiluminescence Detection

The whole chemiluminescence setup depicted in FIG. 32 was set up in a dark box made out of foam board and aluminum tape. The darkness of the box was checked using the PMT such that the background current obtained was around 3 nano Amperes. Since the signals that are emitted from the reaction between the enzyme and the substrate are pretty low even a small streak of stray light caused a major difference in the signal. Hence the box was built in a very robust manner such that it is completely light tight. The box was setup with a CCD camera to record the droplet motion (FIG. 32).

8.9.3 Experimental Protocol (on Chip)

Figure 33:
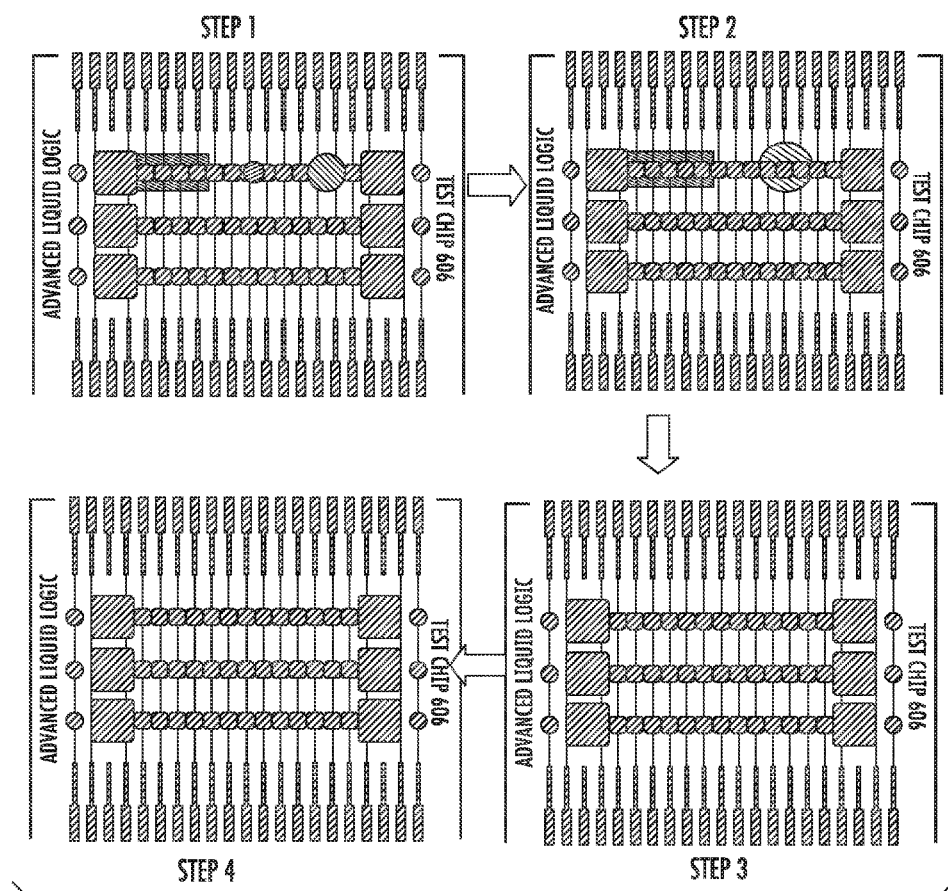
FIG. 33 is an illustration of an experimental protocol for magnetic immunoassay on a digital microfluidic platform.

FIG. 33 depicts an experimental protocol for magnetic immunoassay on a digital microfluidic platform. 1 µl of the anti insulin antibody coupled with the magnetically responsive beads was mixed with 1 µl of anti insulin antibody labeled with ALP enzyme to form a 2 µl mixture in a tube. Since the ALP enzyme has the tendency to adsorb to the magnetic beads and enhance the secondary signal 1 µl of blocking IgG was added to form a 3 µl of mixture. This mixture of the three antibodies was pipetted on an electrode on the Test chip 606.

1 µl of a known concentration of insulin sample was pipetted on another electrode in the same array on the chip. Both these droplets were sandwiched using an ITO and Teflon coated top plate and the gap was filled with 1.5 cSt silicone oil.

Figure 34B:
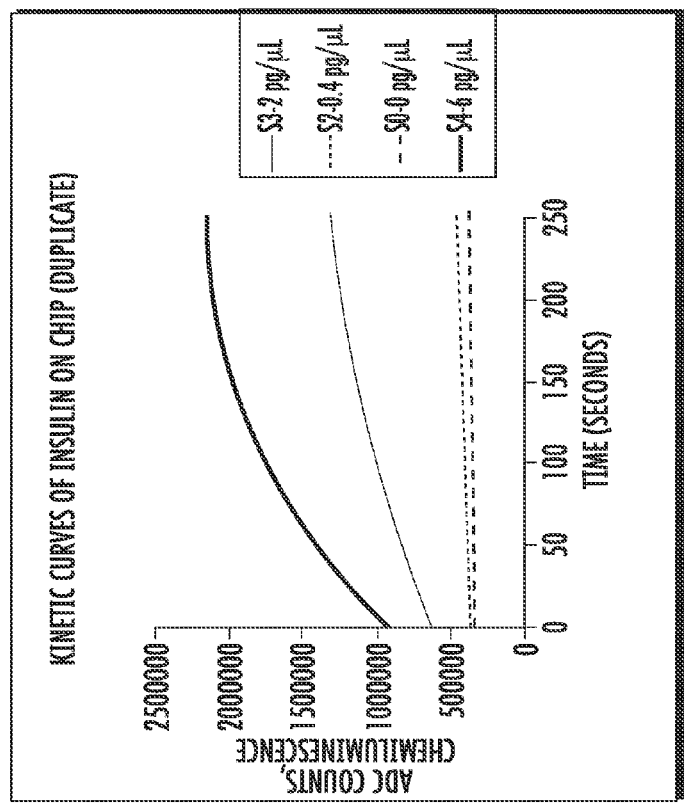
FIGS. 34A and 34B are graphical illustrations of kinetic curves of different concentrations of insulin (magnetic immunoassay)
Figure 34A:
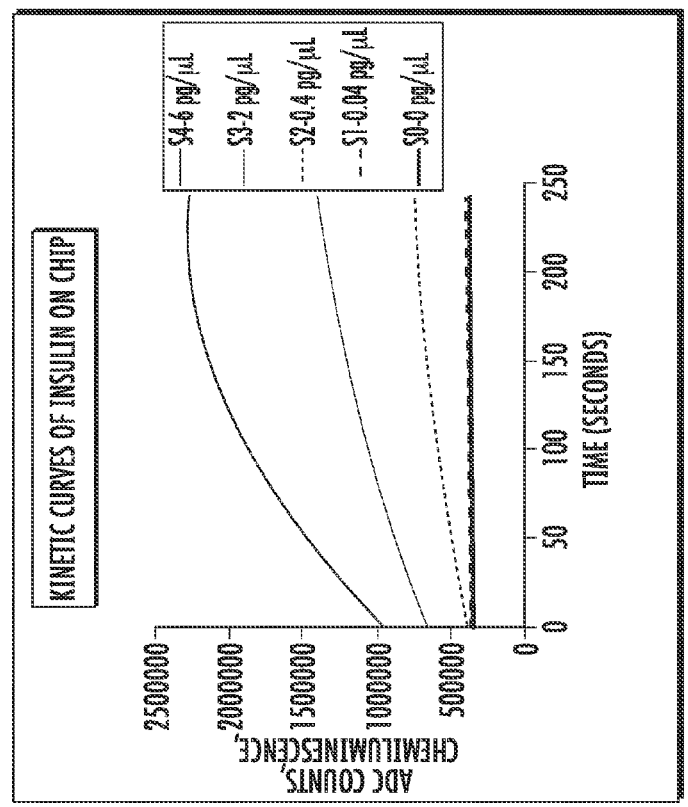

A gap height of 300 µm was maintained. The droplets were brought closer to each other using electrowetting and merged and allowed to incubate for 1 minute. Washing of the magnetic beads was done with the washing protocol developed earlier to remove the excess supernatant. 4 µl of wash buffer was used to dilute the supernatant for each wash. The beads were washed 5 times with 4 µl of wash buffer each time which gave 4^5 dilution to the supernatant surrounding the beads. Then the beads were resuspended in the solution surrounding the beads by agitating the droplet using electrowetting. This resuspended the beads and avoided any clumping. 2 µl of Lumigen APS 5 substrate was added and the chemiluminescence was read for every 1 second using the photomultiplier tube (PMT) set up in the dark box for a span of 4 minutes. FIG. 34 shows kinetic curves for concentrations of 0, 0.04, 0.4, 2, 6 pg/µl. However to obtain a standard curve (FIG. 34) of the signal versus the insulin concentrations, the area under each curve was calculated for each concentration and plotted against the insulin concentrations. The same experiment was repeated thrice on different days and the results were reproducible with an error of less than 3%. Thus a magnetic immunoassay on insulin was performed on a digital microfluidic platform with multiple operations like merging of droplets, splitting, washing of magnetic beads which involved immobilization of beads within the droplet and resuspension of beads and on chip detection.

The assay was reproducible with an error of less than 3% between different runs on different days. It can be seen from the above curve that concentration of insulin as low as 0.4 pg/μl was detected using the magnetic immunoassay. The sensitivity can further be improved by reducing the distance between the PMT and the droplet. However to validate the data obtained on chip, the same experiment was repeated on bench with every step performed on bench in tubes.

8.9.4 Experimental Protocol (on Bench)

Figure 35:
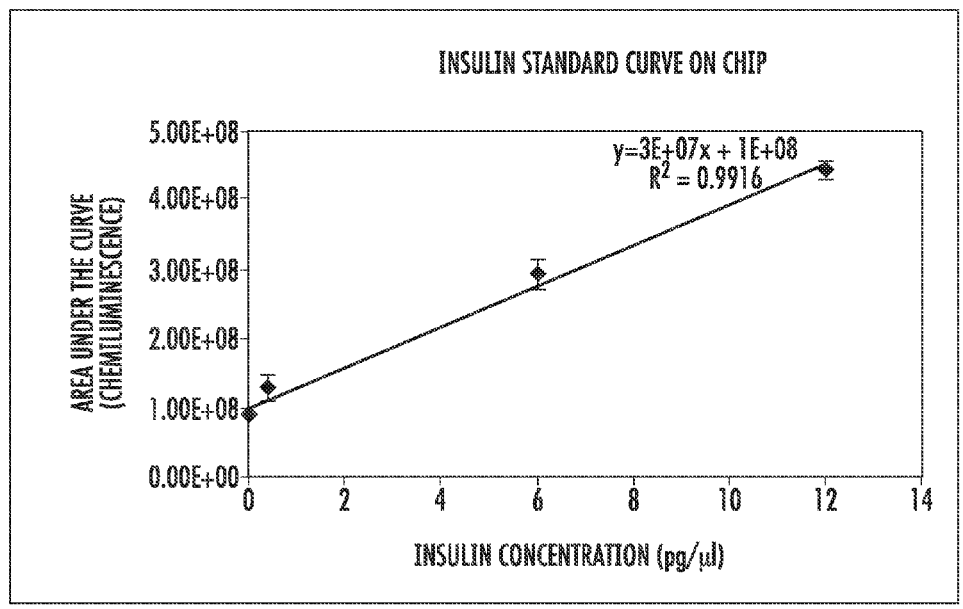
FIG. 35 is a graphical illustration of an insulin standard curve on chip.

The same experiment described in the above section was repeated on bench in tubes to validate the data obtained on chip. 1 μl of anti-insulin antibody labeled with magnetic beads was mixed with 1 μl of anti-insulin antibody labeled with ALP enzyme to which 1 μl of blocking IgG was added. A 1 μl sample of a known concentration of insulin was added to the above mixture and allowed to incubate for 5 minutes in the tube. The excess/unreacted supernatant was later removed by immobilizing the magnetic beads using a 1 Tesla magnet. The beads were then washed 5 times with 4 μl sample of wash buffer each time. Later the beads were resuspended in 1 μl of wash buffer and a 2 μl of Lumigen APS 5 substrate for the ALP enzyme was added and the chemiluminescence was read under the same conditions that were done on chip. The chemiluminescence readings were taken every second for a span of 4 minutes and similar analysis was done as described above. The areas under each kinetic curve (FIG. 34) were calculated and plotted against corresponding concentration of insulin to obtain the following standard curve (FIG. 35). It can be seen that the standard curve obtained on chip is very comparable with the standard curve obtained on bench. The background obtained for the zero concentration of insulin was exactly the same as obtained on chip which reinstates that the washing on chip was very good. Hence a magnetic immunoassay with a detection sensitivity of 0.8 pg/μl was performed on a digital microfluidic platform.

8.10 Insulin Assay on Serum

Materials—Serum with an unknown concentration of insulin obtained from Sigma, Insulin standard (12 pg/μL) from Beckmann Coulter Inc., anti-insulin antibody coupled with magnetic beads (reagent A), anti-insulin antibody labeled with alkaline phosphatase enzyme (reagent B) and blocking antibody (reagent C) from the Access® immunoassay kit from Beckmann Coulter Inc., Access® wash buffer diluted 10 times by a buffer with 0.5M Tris and 0.01 M NaCl, Lumigen APS-5 substrate for alkaline phosphatase, 1.5 cSt Silicone oil, Test chip 606 coated with 5 μm parylene and coated with 1% Teflon, ITO coated glass plate coated with 1% Teflon which acts as a ground electrode.

Methods—Insulin assay was performed following the same protocol as depicted above. However the analyte was not insulin standards prepared in buffer but human serum whose insulin concentration is unknown. Aliquots of serum were thawed and doped with insulin by mixing 1 part of insulin standard (12 pg/μL) with 4 parts of serum and 1 part of insulin standard (12 pg/μL) with 9 parts of serum. The complete immunoassay was performed with 4 standards which included 0 pg/μL concentration of insulin. The chemiluminescence was collected with the help of a PMT placed right over the droplet and measured in terms of ADC counts.

Figure 36:
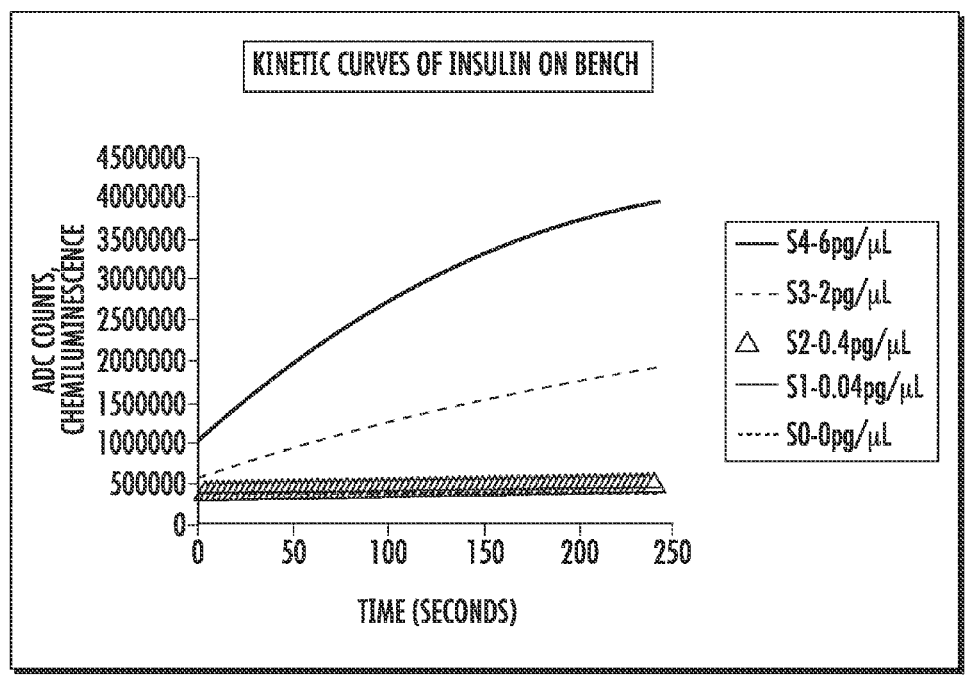
FIG. 36 is a graphical illustration of kinetic curves for different concentrations of insulin (on bench)
Figure 37:
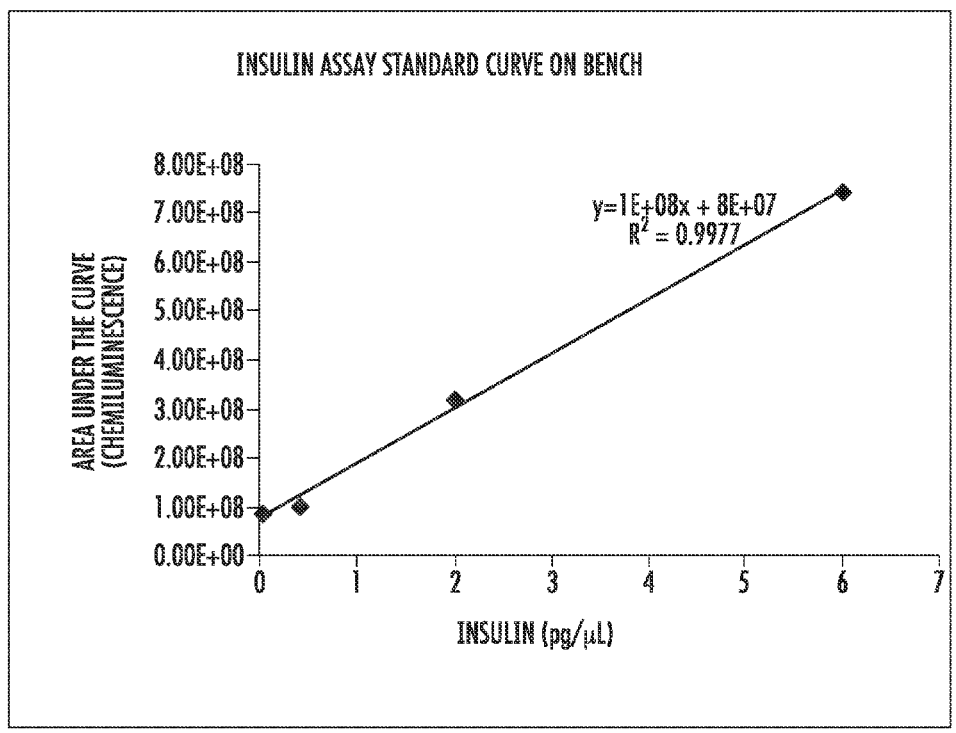
FIG. 37 is a graphical illustration of an insulin standard curve on bench.

Inference—It can be observed from the kinetic curves (FIG. 36) that the chemiluminescent signal increases with the increase in insulin concentration. The insulin concentration in the serum was calculated by utilizing the standard curve on chip obtained earlier and it was found that the serum had 0.2 pg/μL of insulin concentration. The kinetic curves were as shown in the figure.

8.11 Magnetic Immunoassay of Interleukin-6 (IL-6) on Chip

Interleukin-6 is a multi functional protein that regulates the immune response, acute phase reactions, and hematopoiesis. IL-6 is produced by lymphoid and non-lymphoid cells, and by normal and transformed cells, including T cells, B cells, monocytes, fibroblasts, vascular endothelial cells, cardiac myxomas, bladder cell carcinomas, myelomas, astrocytomas and glioblastomas. The production of IL-6 in these various cells is regulated either positively or negatively by a variety of signals including mitogens, antigenic stimulation, lipopolysaccharides, IL-1 and viruses. On the basis of its various activities, IL-6 has also been called interferon-β (IFN-β2), 26 kDa protein, B-cell stimulatory factor-2 (BSF-2), hybridoma/plasmacytoma growth factor, hepatocyte stimulating factor, and macrophage-granulocyte inducing factor 2A (MGI-2A). A lot of reviews have been published on interleukin-6 [Kishimoto, 1992; Hirano, 1990; Hirano, 1992; Hirano, 1990]. Disruption of IL-6 regulation might affect the immune response and consequently induce the immune-mediated inflammatory diseases such as rheumatoid arthritis, systemic juvenile idiopathic arthritis, Castleman disease and Crohn's disease. Over production of IL-6 [Nishimoto, 2006] also contributes to the development of malignant diseases such as multiple myeloma and renal cancer. These proteins exist in really low concentrations in the blood of the diseased and require very sensitive assays to detect such low concentrations.

8.11.1 Immunoassay of IL-6 on Digital Microfluidic Chip

Materials—Access® IL-6 reagent pack (cat# A 30945). The pack contains the following reagents.

TABLE 1

| R1a | Paramagnetic particles coated with goat anti-mouse IgG: mouse antihuman IL-6 monoclonal antibody, BSA, surfactant, 0.1% sodium azide and 0.17% Proclin 300 |
|---|---|
| R1b | Tris saline buffer, proteins (porcine, goat, bovine, mouse), surfactant, 0.1% sodium azide and 0.17% Proclin 300 |
| R1c | Goat anti-human IL-6 alkaline phosphatase(bovine) conjugate, BSA, surfactant, 0.1% sodium azide and 0.17% Proclin 300 |

Lumigen APS-5 substrate from Lumigen Inc. for alkaline phosphatase, 1.5 cSt silicone oil with 0.1% Triton X-15, Glass chip coated with 5 μm parylene and dip coated with 1% Teflon, ITO coated glass plate dip coated with 1% Teflon which acts as the ground plane.

Methods—The immunoassay on the glass chip was performed following the same protocol as depicted above. 1 μL each of R1a, R1b and R1c were pipetted manually on to an electrode on the chip and 1 μL of the IL-6 sample was pipetted at different electrode on the same electrode array. Both these droplets were sandwiched by placing a ITO coated glass plate over the droplets which acts as the ground plane. A gap height of 300 μm was maintained which was filled with 1.5 cSt silicon oil with 0.1% Triton® X 15. Both the droplets were merged using electrowetting and allowed to incubate for 2 minutes with agitation performed by transporting over 4-5 electrodes. The whole reaction mixture was taken to the electrode with the 1 Tesla magnet underneath and the supernatant was removed using the washing protocol described earlier in the chapter. Washing was performed repetitively until no signal was seen in the supernatant using 4 μL wash samples for each wash. 2 μL of the substrate (Lumigen APS-5) was added to the washed magnetic beads and the chemiluminescence was collected with a PMT placed right over the droplet for 4 minutes in terms of ADC counts.

Figure 38:
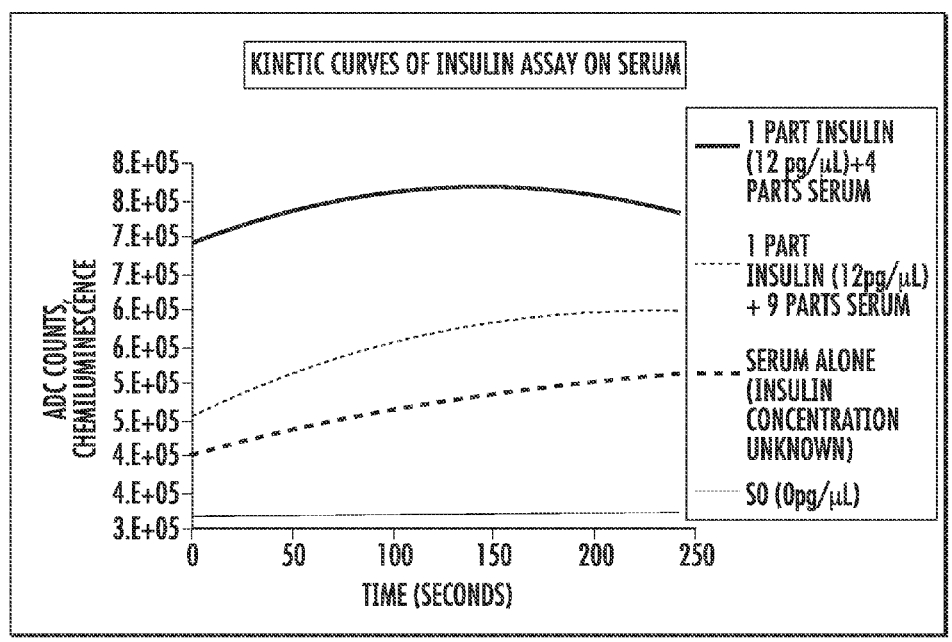
FIG. 38 is a graphical illustration of kinetic curves of insulin assay on serum.
Figure 39:
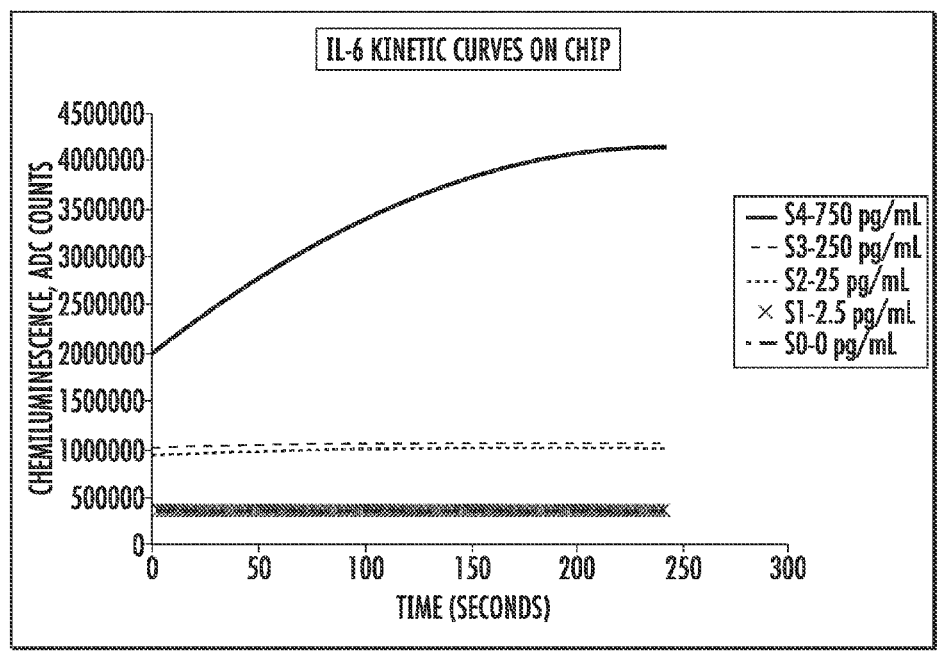
FIG. 39 is a graphical illustration of kinetic curves of IL-6 immunoassay on lab-on-a-chip.
Figure 40:
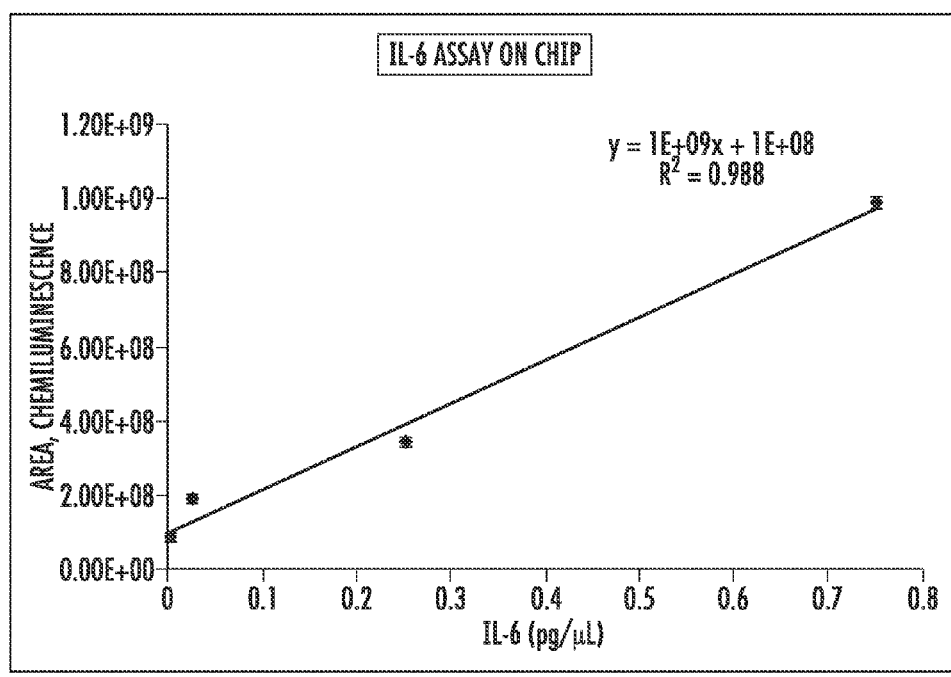
FIG. 40 is a graphical illustration of a standard curve of IL-6 immunoassay on lab-on-a-chip.

Analysis—The kinetic curves were plotted as chemiluminescence in terms of ADC counts versus time in seconds shown in FIGS. 38 and 39. The area under each kinetic curve was calculated by integrating the curve for 240 seconds and the area for each concentration was plotted against the concentration to obtain a standard curve on chip as shown in FIG. 40. It can be observed that the lowest concentration of IL-6 that can be detected using this droplet based lab-on-a-chip magnetic immunoassay is 0.025 pg/µL. The data was reproducible with a standard error of less than 2%.

A protocol for effectively washing the magnetic beads on droplet based lab-on-a-chip was developed. Optimal strength, position of the magnet was simulated and experimentally determined to effectively immobilize all the magnetically responsive beads without aggregation and resuspend substantially all the beads after washing. The washing protocol developed provided a bead retention of approximately 99.9995%. Magnetic immunoassays were performed on insulin and IL-6 on this droplet based lab-on-a-chip utilizing the washing protocol developed. The sensitivities achieved were 0.4 pg/µL for insulin and 0.025 pg/µL for IL-6. The data obtained was very much comparable with the data obtained on bench and is very reproducible for separate runs on different days.

8.12 Droplet Actuator

For examples of droplet actuator architectures that are suitable for use with the present invention, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; and International Patent Application No. PCT/US 06/47486 to Pollack et al., entitled "Droplet-Based Biochemistry," filed on Dec. 11, 2006, the disclosures of which are incorporated herein by reference. Droplet actuator techniques for immobilizing magnetic beads and/or non-magnetic beads are described in the foregoing international patent applications and in Sista, et al., International Patent Application No. PCT/US 08/53545, filed on Feb. 11, 2008, entitled "Droplet Actuator Devices and Methods Employing Magnetic Beads"; Sista et al., U.S. Patent Application No. 60/969,736, filed on Sep. 4, 2007, entitled "Droplet Actuator Assay Improvements"; and Allen et al., U.S. Patent Application No. 60/957,717, filed on Aug. 24, 2007, entitled "Bead washing using physical barriers," the entire disclosures of which is incorporated herein by reference. Combinations of these various techniques are within the scope of this invention.

8.13 Fluids

For examples of fluids that may be subjected to droplet operations of the invention, see the patents listed in section 8.12, especially International Patent Application No. PCT/US 06/47486, entitled, "Droplet-Based Biochemistry," filed on Dec. 11, 2006. In some embodiments, the droplet is a sample fluid, such as a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, fluidized tissues, fluidized organisms, biological swabs and biological washes. In some embodiments, the fluid that is loaded includes a reagent, such as water, deionized water, saline solutions, acidic solutions, basic solutions, detergent solutions and/or buffers. In some embodiments, the fluid that is loaded includes a reagent, such as a reagent for a biochemical protocol, such as a nucleic acid amplification protocol, an affinity-based assay protocol, a sequencing protocol, and/or a protocol for analyses of biological fluids.

8.14 Filler Fluids

The gap will typically be filled with a filler fluid. The filler fluid may, for example, be a low-viscosity oil, such as silicone oil. Other examples of filler fluids are provided in International Patent Application No. PCT/US 06/47486, entitled "Droplet-Based Biochemistry," filed on Dec. 11, 2006.

9 Conclusion

The invention relates to the design and prototyping of a lab-on-a-chip for immunoassays. Further, the invention relates to a protocol for effectively washing the magnetic beads. The biocompatibility of the droplet based electrowetting platform was established by transporting different proteins applicable in an immunoassay including the mobilization of magnetically responsive beads which does not exist in any of the commercially available immunoassay analyzers. The insulator breakdown which caused catastrophic failures and ultimately determined the lifetime of the chip and duration of experiments was resolved by using a thicker parylene and Teflon AF coatings. The protein fouling on the lab-on-a-chip was partially quantified. Hence the lab-on-a-chip fabricated is capable of performing all the basic fluidic operations such as droplet dispensing, transport, mixing and splitting.

10 Concluding Remarks

The foregoing detailed description of embodiments refers to the accompanying drawings, which illustrate specific embodiments of the invention. Other embodiments having different structures and operations do not depart from the scope of the present invention.

The term "the invention" is used with reference to certain specific examples of the many alternative aspects or embodiments of the applicants' invention set forth in this specification, and neither its use nor its absence is intended to limit the scope of the applicants' invention or the scope of the claims.

This specification is divided into sections for the convenience of the reader only. Headings should not be construed as limiting of the scope of the invention.

It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A method of providing a droplet in contact with a surface of a super paramagnetic bead with a reduced concentration of a substance, the method comprising:
   (a) providing a paramagnetic bead in contact with a droplet comprising a starting concentration and starting quantity of the substance and having a starting volume;
   (b) conducting one or more droplet operations to merge a wash droplet with the droplet provided in step (a) to yield a combined droplet; and
   (c) conducting one or more droplet operations to divide the combined droplet to yield a set of droplets comprising:
      (i) a droplet in contact with the paramagnetic bead having a decreased concentration of the substance relative to the starting concentration; and (ii) a droplet which is separated from the paramagnetic bead and wherein the droplet operations are electrowetting-mediated.

2. The method of claim 1 wherein step 1(c) yields a droplet in contact with the surface having a decreased quantity of the substance relative to the starting quantity.

3. The method of claim 1 wherein step 1(c) yields a droplet in contact with the surface having a substantially decreased quantity of the substance relative to the starting quantity.

4. The method of claim 1 wherein step 1(c) yields a droplet in contact with the surface having a substantially decreased concentration of the substance relative to the starting concentration.

5. The method of claim 1 wherein step 1(c) yields a droplet in contact with the surface having a volume which is approximately the same as the starting volume.

* * * * *

UNITED STATES PATENT AND TRADEMARK OFFICE
CERTIFICATE OF CORRECTION

| | | |
|---|---|---|
| PATENT NO. | : 8,685,754 B2 | Page 1 of 1 |
| APPLICATION NO. | : 12/393534 | |
| DATED | : April 1, 2014 | |
| INVENTOR(S) | : Michael G. Pollack et al. | |

It is certified that error appears in the above-identified patent and that said Letters Patent is hereby corrected as shown below:

In the Claims

At column 22, delete Lines 54-56, and replace with the following:

-- 1. A method of providing a droplet in contact with a surface of a paramagnetic bead with a reduced concentration of a substance, the method comprising: --

Signed and Sealed this
Thirtieth Day of December, 2014

Michelle K. Lee
*Deputy Director of the United States Patent and Trademark Office*